(12) United States Patent
Kishimura et al.

(10) Patent No.: US 9,051,437 B2
(45) Date of Patent: Jun. 9, 2015

(54) ELECTROSTATICALLY BONDED VESICLE

(75) Inventors: Akihiro Kishimura, Tokyo (JP); Kazunori Kataoka, Tokyo (JP); Stephanie Lee, Tokyo (JP); Yasutaka Anraku, Tokyo (JP); Aya Koide, Hino (JP); Mitsuru Sakai, Tokyo (JP); QiuMing Yu, Hino (JP)

(73) Assignees: THE UNIVERSITY OF TOKYO, Tokyo (JP); TEIJIN LIMITED, Osaka-Shi (JP)

( * ) Notice: Subject to any disclaimer, the term of this patent is extended or adjusted under 35 U.S.C. 154(b) by 0 days.

(21) Appl. No.: 13/812,383

(22) PCT Filed: Jul. 27, 2011

(86) PCT No.: PCT/JP2011/067138
§ 371 (c)(1),
(2), (4) Date: Jan. 25, 2013

(87) PCT Pub. No.: WO2012/014942
PCT Pub. Date: Feb. 2, 2012

(65) Prior Publication Data
US 2013/0122103 A1 May 16, 2013

(30) Foreign Application Priority Data
Jul. 28, 2010 (JP) .................... 2010-168880

(51) Int. Cl.
| | |
|---|---|
| *A61K 9/00* | (2006.01) |
| *C08L 77/04* | (2006.01) |
| *C08L 71/02* | (2006.01) |
| *C08G 81/00* | (2006.01) |
| *A61K 9/127* | (2006.01) |
| *A61K 9/16* | (2006.01) |
| *C08G 69/10* | (2006.01) |
| *C08G 73/02* | (2006.01) |

(52) U.S. Cl.
CPC ............ *C08G 81/00* (2013.01); *Y10T 428/2989* (2015.01); *A61K 9/1273* (2013.01); *C08L 77/04* (2013.01); *C08L 2205/02* (2013.01); *A61K 9/1641* (2013.01); *C08G 69/10* (2013.01); *C08G 73/0233* (2013.01)

(58) Field of Classification Search
None
See application file for complete search history.

(56) References Cited

U.S. PATENT DOCUMENTS

| | | | | |
|---|---|---|---|---|
| 6,835,394 | B1* | 12/2004 | Discher et al. ............... | 424/450 |
| 8,304,497 | B2* | 11/2012 | Kataoka et al. ............... | 525/403 |
| 8,415,400 | B2* | 4/2013 | Bronich et al. ............. | 514/772.1 |
| 2009/0325171 | A1* | 12/2009 | Hirt et al. ......................... | 435/6 |
| 2013/0202711 | A1 | 8/2013 | Kataoka et al. | |

FOREIGN PATENT DOCUMENTS

| | | |
|---|---|---|
| EP | 0 721 776 A1 | 7/1996 |
| EP | 1230934 A1 | 8/2002 |
| EP | 18788766 A1 | 1/2008 |
| EP | 2284210 A1 | 2/2011 |
| EP | 2 572 780 A1 | 3/2013 |
| JP | 08-188541 A | 7/1996 |
| JP | 2001-146556 A | 5/2001 |
| WO | WO 2006/118260 A1 | 11/2006 |
| WO | WO 2009/133968 A1 | 11/2009 |
| WO | WO 2011/145745 A1 | 11/2011 |

OTHER PUBLICATIONS

"Spontaneous Formation of Nanosized Unilamellar Polyion Complex Vesicles with Tunable Size and Properties" authored by Anraku et al. and published in JACS (2010) 132, 1631-1636.*
"Stabilization of Peptide Vesicles by Introducing Inter-Peptide Disulfide Bonds" authored by van Hell et al., and published in Pharmaceutical Research (2009) 26(9), 2186-2193.*
PCT/ISA/210—International Search Report mailed on Oct. 25, 2011, issued in PCT/JP2011/067138.
PCT/ISA/220—mailed on Oct. 25, 2011, issued in PCT/JP2011/067138.
PCT/ISA/237—mailed on Oct. 25, 2011, issued in PCT/JP2011/067138.
Kishimura et al., "Precise control of morphology of polyion complexes (PICs) by tuning of PEG fraction in PICs and evaluation of their functions", Polymer Preprints, vol. 58, No. 2 (2009) pp. 2917-2918.
Matsuda et al., "Size control and fixation by cross-linking of PEGylated polyion complex vesicles (PICsomes) prepared from a pair of oppositely charged block ionomers", Polymer Preprints, vol. 567, No. 1 (2008) p. 1036.
Extended European Search Report dated Mar. 18, 2014 issued for European Patent Application No. 11812531.9.
Kishimura, et al., PICSome Technology: Polymeric Vesicles Toward Biomedical Applications, 2009, Artificial Blood, vol. 17, No. 2, pp. 73-81.
Schlaad, et al., Macromolecules, Mar. 11, 2003, American Chemical Society, vol. 36, No. 5, pp. 1417-1420.
Yow, et al., Formation of Liquid Core-Polymer Shell Microcapsules, 2006, The Royal Society of Chemistry, pp. 940-949.

* cited by examiner

*Primary Examiner* — Marc Zimmer
(74) *Attorney, Agent, or Firm* — Birch, Stewart, Kolasch & Birch, LLP

(57) ABSTRACT

The purpose of the present invention is to provide an electrostatically bonded vesicle which bears disulfide bonds or thiol groups. The present invention relates to a vesicle having a membrane which is formed from both a first polymer of (a) or (b) and a second polymer of (c) or (d) (with the proviso that a combination of (b) and (d) is excepted) and in which the cationic segment and anionic segment of the polymers are partially crosslinked. First polymer: (a) a block copolymer (I) having both an electrically non-charged hydrophilic segment and a cationic segment, (b) an amino acid polymer (I) having a cationic segment. Second polymer: (c) a block copolymer (II) having both an electrically non-charged hydrophilic segment and an anionic segment, (d) an amino acid polymer (II) having an anionic segment.

12 Claims, 11 Drawing Sheets

(a)

(b)

ELECTROSTATICALLY BONDED VESICLE

TECHNICAL FIELD

The present invention relates to a vesicle formed from water-soluble and charged polymers. More specifically, the present invention relates to an electrostatically bonded vesicle comprising polymers bearing thiol groups or disulfide groups, which has useful functions as a drug delivery system and a material for various uses.

BACKGROUND ART

It is known that polymers in which the primary structure is precisely controlled may be spontaneously assembled to form a higher-order structure. Specific examples thereof include structures such as micelles and vesicles. In the case of such a structure in which polymers are self-assembled, various types of molecules can be designed, and in addition to characteristics originally had by the polymers, new functions may be had by the structure. Utilization of such structures in which polymers are self-assembled has been examined in various fields such as those of the drug delivery system and material science.

For example, Japanese Laid-Open Patent Publication No. H08-188541 (Patent Document 1) discloses an electrostatically-bonded polymer micelle drug carrier made of a block copolymer having a non-charged segment and a charged segment. Further, WO2006/118260 (Patent Document 2) discloses, as an electrostatically-bonded vesicle, a vesicle composed of a membrane formed by interaction between two copolymers.

Further, Helmut Schlaad et al., Macromolecules, 2003, 36(5), 1417-1420 (Non-Patent Document 1) discloses that a vesicle called a polymersome can be formed using a block copolymer composed of a poly(1,2-butadiene) block and a poly(cesium methacrylate) block and a block copolymer composed of a polystyrene block and a poly(1-methyl-4-vinylpyridium iodide) block.

Though it is expected that a structure formed from a polymer material has excellent availability, it is often required to use an organic solvent such as chloroform at the time of the production. Moreover, at the time of the production of a structure in which a polymer material is self-assembled, complicated operation comprising a plurality of steps may be required. Therefore, it can be said that it is desired to create a structure having availability which can be produced by simple operation.

In Anraku Y. et al., J. Am. Chem. Soc., 2010, 132(5), 1631-1636 (Non-Patent Document 2), a vesicle made by self-assembly of a block copolymer having an electrically non-charged hydrophilic segment and a charged segment (e.g., polyethylene glycol (PEG)-polyanion) and a copolymer having an electric charge which is opposite to that of the charged segment (e.g., polycation) is disclosed by a part of the present inventors. According to this technique, only by mixing two types of polymer aqueous solutions, a vesicle made of one electrostatically-bonded membrane with a uniform diameter of 100 to 400 nm can be conveniently produced. It is usually considered that a vesicle obtained by self-assembly of polymers is allowed to include/carry various substances in its hollow and to release the included things under appropriate circumstances for use (for the outline, see: H. Nyin et al., Soft Matter, 2006, 2, 940-949 (Non-Patent Document 3); "Riposomu Ouyou no Shin-tenkai (New development of application of liposome)", Kazunori Akiyoshi et al., ed., NTS, 2005 (Non-Patent Document 4); and Akihiro Kishimura and Kazunori Kataoka, "Jinko Ketsueki (Artificial blood)", 2009, 17, 73-81 (Non-Patent Document 5)). Therefore, regarding the above-described electrostatically-bonded vesicle, it is desired to establish a convenient crosslinking method and a method of controlling the release property and stability of the vesicle in an environmentally-responsive manner.

CITATION LIST

Patent Documents

Patent Document 1: Japanese Laid-Open Patent Publication No. H08-188541
Patent Document 2: WO2006/118260

Non-Patent Documents

Non-Patent Document 1: Helmut Schlaad et al., Macromolecules, 2003, 36(5),
Non-Patent Document 2: Anraku Y. et al., J. Am. Chem. Soc., 2010, 132(5), 1631-1636
Non-Patent Document 3: H. Nyin et al., Soft Matter, 2006, 2, 940-949
Non-Patent Document 4: "Riposomu Ouyou no Shin-tenkai (New development of application of liposome)", Kazunari Akiyoshi and Kaoru Tsujii, ed., NTS, 2005
Non-Patent Document 5: Akihiro Kishimura and Kazunori Kataoka, "Jinko Ketsueki (Artificial blood)", 2009, 17, 73-81

SUMMARY OF INVENTION

Technical Problem

The purpose of the present invention is to provide a vesicle formed from water-soluble and charged polymers.

Solution to Problem

The present inventor diligently made researches in order to solve the above-described problem, and not only found that by introducing thiol groups and/or disulfide groups into water-soluble and charged block copolymers, a vesicle comprising a charged segment portion can be conveniently prepared, but also found a technique in which a stabilized vesicle can be obtained by crosslinking and a crosslinked structure portion can be cleaved in an environmentally-responsive manner even after crosslinking of the vesicle. Thus the present invention was achieved.

That is, the present invention relates to a vesicle having a membrane which is formed from both a first polymer of (a) or (b) and a second polymer of (c) or (d) (with the proviso that a combination of (b) and (d) is excepted) and in which the cationic segment and anionic segment of the polymers are partially crosslinked.
First Polymer:
(a) a block copolymer (I) having both an electrically non-charged hydrophilic segment and a cationic segment
(b) an amino acid polymer (I) having a cationic segment
Second Polymer:
(c) a block copolymer (II) having both an electrically non-charged hydrophilic segment and an anionic segment
(d) an amino acid polymer (II) having an anionic segment
In the present invention, a crosslinked site has a structure including disulfide bonds.

Further, in another embodiment of the present invention, the aforementioned membrane has a three-layer structure consisting of an outer layer, an intermediate layer and an inner layer, wherein the outer layer and the inner layer are composed of the electrically non-charged hydrophilic segment and the intermediate layer is composed of the cationic segment and the anionic segment.

Examples of the electrically non-charged hydrophilic segment include polyethylene glycol and/or poly(2-oxazoline).

Examples of the cationic segment include those represented by the following formula (1):

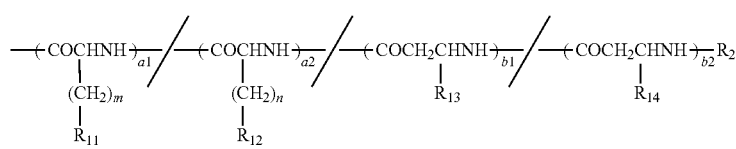

(1)

wherein: $R_2$ represents a hydrogen atom, an acetyl group, a trifluoroacetyl group, an acryloyl group or a methacryloyl group;

$R_{11}$ and $R_{13}$ each independently represent —$(CH_2)_3NH_2$ or —$CONH(CH_2)_s$—$X_1$, wherein: s is an integer from 0 to 20; and $X_1$ is at least one selected from the group consisting of —$NH_2$, a pyridyl group, a morpholyl group, a 1-imidazolyl group, a piperazinyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group, a piperidinyl group, a guanidino group, a diisopropylamino group, a dimethylamino group, a diethylamino group, —$(CH_2)_tNH_2$ and —$(NR_9(CH_2)_o)_pNHR_{10}$, wherein: $R_9$ represents a hydrogen atom or a methyl group; $R_{10}$ represents a hydrogen atom, an acetyl group, a trifluoroacetyl group, a benzyloxycarbonyl group, —$C(=NH)$—$NH_2$ or a tert-butoxycarbonyl group; o is an integer from 1 to 15; p is an integer from 1 to 5; and t is an integer from 0 to 15;

$R_{12}$ and $R_{14}$ each independently represent a thiol group (—SH group), a $C_{1-42}$ alkyl group including a thiol group, —$SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —$CONH(CH_2)_s$—$X_2$, wherein: s is an integer from 0 to 20; and $X_2$ is at least one selected from the group consisting of a thiol group, a $C_{1-12}$ alkyl group including a thiol group, $SR_{30}$ ($R_{30}$ is the same as above), and a pyridyl group, a 1-imidazolyl group, a piperazinyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group and a piperidinyl group, which are substituted with a thiol group, a $C_{1-12}$ alkyl group including a thiol group or $SR_{30}$ ($R_{30}$ is the same as above), and —S—S—$(CH_2)_tNH_2$, —S—S—$(NR_9(CH_2)_o)_pNHR_{10}$, —$(CH_2)_tNHCO(CH_2)_u$SH and —$(CH_2)_tNHC(=NH)(CH_2)_vSH$, wherein $R_9$, $R_{10}$, o, p and t are the same as above, u is an integer from 0 to 15, and v is an integer from 0 to 15;

m and n are 1 or 2;

a1 and a2 are an integer from 0 to 5,000, b1 and b2 are an integer from 0 to 5,000, and a1+a2+b1+b2 is 2 to 5,000; and "/" means that the sequence order of monomer units is arbitrary.

In this specification, o is an integer from 1 to 15, and preferably an integer from 1 to 10.

In this specification, s is an integer from 0 to 20, and preferably an integer from 2 to 8.

Preferably, in the above-described formula (1):

$R_{11}$ and $R_{13}$ are each independently —$CONH(CH_2)_s$—$NH_2$ (s is an integer from 2 to 8);

$R_{12}$ and $R_{14}$ are each independently a thiol group, —$CONH(CH_2)_s$—S—S—$(CH_2)_tNH_2$, —$CONH(CH_2)_s$—SH, —$CONH(CH_2)_sNHCO(CH_2)_uSH$ or —$CONH(CH_2)_s$NHC($=$NH)$(CH_2)_vSH$ (s is an integer from 2 to 8, t is an integer from 0 to 15, u is an integer from 1 to 8, and v is an integer from 1 to 8);

$R_2$ is a hydrogen atom;

a1 and a2 are an integer from 0 to 200, b1 and b2 are an integer from 0 to 200, and a1+a2+b1+b2 is 10 to 200.

In the present invention, examples of the anionic segment include those represented by the following formula (2):

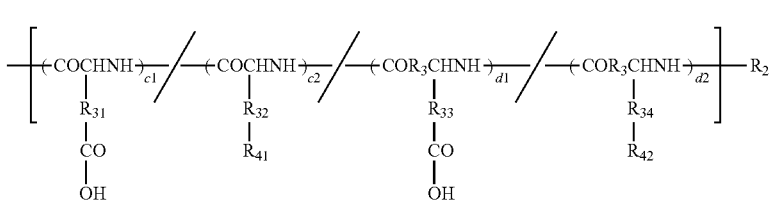

(2)

wherein: $R_2$ represents a hydrogen atom, an acetyl group, a trifluoroacetyl group, an acryloyl group or a methacryloyl group;

$R_3$s each independently represent a methylene group or an ethylene group;

$R_{31}$ and $R_{32}$ each independently represent a methylene group or an ethylene group;

$R_{33}$ and $R_{34}$ each independently represent a single bond, or a methylene group or an ethylene group;

$R_{41}$ and $R_{42}$ each independently represent a benzyloxycarbonyl group, a thiol group, a $C_{1-12}$ alkyl group including a thiol group, —$SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —$CONH(CH_2)_s$—$X_3$, wherein s is an integer from 0 to 20, and $X_3$ is a thiol group, a $C_{1-12}$ alkyl group including a thiol group or —$SR_{30}$ ($R_{30}$ is the same as above);

c1 and c2 are an integer from 0 to 5,000, d1 and d2 are an integer from 0 to 5,000, and c1+c2+d1+d2 is 2 to 5,000; and "/" means that the sequence order of monomer units is arbitrary.

Preferably, in the above-described formula (2): $R_2$ represents a hydrogen atom; $R_3$ represents a methylene group; $R_{31}$, $R_{32}$, $R_{33}$ and $R_{34}$ represent a methylene group; $R_{41}$ and $R_{42}$ are a thiol group or —CONH(CH$_2$)$_s$—SH (S is an integer from 2 to 8); c1 and c2 are an integer from 0 to 200, d1 and d2 are an integer from 0 to 200, and c1+c2+d1+d2 is 10 to 200.

In the present invention, examples of the block copolymer (I) include those represented by the following formula (3) or (4):

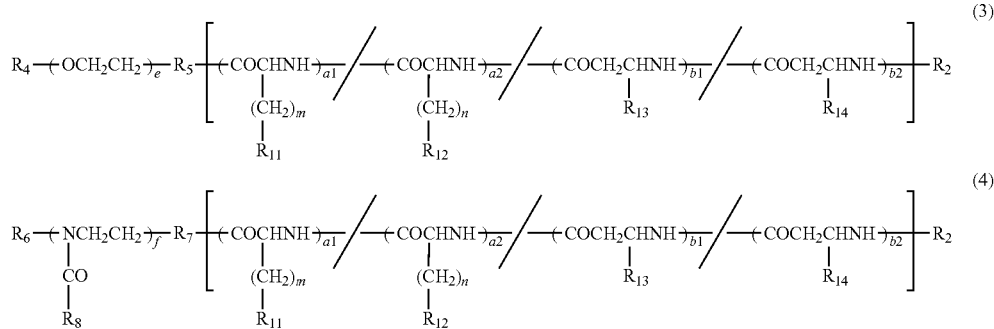

wherein: $R_2$ represents a hydrogen atom, an acetyl group, a trifluoroacetyl group, an acryloyl group or a methacryloyl group;

$R_{11}$ and $R_{13}$ each independently represent —(CH$_2$)$_3$NH$_2$ or —CONH(C$_{1-12}$)$_s$—X$_1$, wherein: s is an integer from 0 to 20; and X$_1$ is at least one selected from the group consisting of —NH$_2$, a pyridyl group, a morpholyl group, a 1-imidazolyl group, a piperazinyl group, a 4-(C$_{1-6}$ alkyl)-piperazinyl group, a 4-(amino C$_{1-6}$ alkyl)-piperazinyl group, a pyrrolidine-1-yl group, a N-methyl-N-phenylamino group, a piperidinyl group, a guanidino group, a diisopropylamino group, a dimethylamino group, a diethylamino group, —(C$_{1-2}$)$_t$NH$_2$ and —(NR$_9$(CH$_2$)$_o$)$_p$NHR$_{10}$, wherein: $R_9$ represents a hydrogen atom or a methyl group; $R_{10}$ represents a hydrogen atom, an acetyl group, a trifluoroacetyl group, a benzyloxycarbonyl group, —C(=NH)—NH$_2$ or a tert-butoxycarbonyl group; o is an integer from 1 to 15; p is an integer from 1 to 5; and t is an integer from 0 to 15;

$R_{12}$ and $R_{14}$ each independently represent a thiol group, a C$_{1-12}$ alkyl group including a thiol group, —SR$_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —CONH(CH$_2$)$_s$—X$_2$, wherein: s is an integer from 0 to 20; and X$_2$ is at least one selected from the group consisting of a thiol group, a C$_{1-12}$ alkyl group including a thiol group, SR$_{30}$ ($R_{30}$ is the same as above), and a pyridyl group, a 1-imidazolyl group, a piperazinyl group, a 4-(C$_{1-6}$ alkyl)-piperazinyl group, a 4-(amino C$_{1-6}$ alkyl)-piperazinyl group, a pyrrolidine-1-yl group, a N-methyl-N-phenylamino group and a piperidinyl group, which are substituted with a thiol group, a C$_{1-12}$ alkyl group including a thiol group or SR$_{30}$ ($R_{30}$ is the same as above), and —S—S—(CH$_2$)$_t$NH$_2$, —S—S—(NR$_9$(CH$_2$)$_o$)$_p$NHR$_{10}$, —(CH$_2$)$_t$NHCO(CH$_2$)$_u$SH and —(CH$_2$)$_t$NHC(=NH)(CH$_2$)$_v$SH, wherein $R_9$, $R_{10}$, o, p and t are the same as above, u is an integer from 0 to 15, and v is an integer from 0 to 15;

m and n are 1 or 2;

$R_4$ represents a hydrogen atom or an optionally substituted linear or branched C$_{1-12}$ alkyl group;

$R_5$ represents —(CH$_2$)$_g$NH— and g is 0 to 5;

$R_6$ and $R_7$ are respectively the same as $R_4$ and $R_5$;

$R_8$ represents a linear or branched C$_{1-12}$ alkyl group;

a1 and a2 are an integer from 0 to 5,000, b1 and b2 are an integer from 0 to 5,000, and a1+a2+b1+b2 is 2 to 5,000;

e is an integer from 5 to 2,500, and f is an integer from 5 to 2,500; and

"/" means that the sequence order of monomer units is arbitrary.

Preferably, in the above-described formula (3) or (4):

$R_{11}$ and $R_{13}$ are each independently —CONH(CH$_2$)$_s$—NH$_2$ (s is an integer from 2 to 8);

$R_{12}$ and $R_{14}$ are each independently a thiol group, —CONH(CH$_2$)$_s$—S—S—(CH$_2$)$_t$NH$_2$, —CONH(CH$_2$)$_s$—SH, —CONH(CH$_2$)$_s$NHCO(CH$_2$)$_u$SH or —CONH(CH$_2$)$_s$NHC(=NH)(CH$_2$)$_v$SH (s is an integer from 2 to 8, t is an integer from 0 to 15, u is an integer from 1 to 8, and v is an integer from 1 to 8);

$R_2$ is a hydrogen atom;

$R_4$ is a methyl group;

a1 and a2 are an integer from 0 to 200, b1 and b2 are an integer from 0 to 200, and a1+a2+b1+b2 is 10 to 200, e is an integer from 10 to 300, and f is an integer from 10 to 300.

In the present invention, examples of the block copolymer (II) include those represented by the following formula (5) or (6):

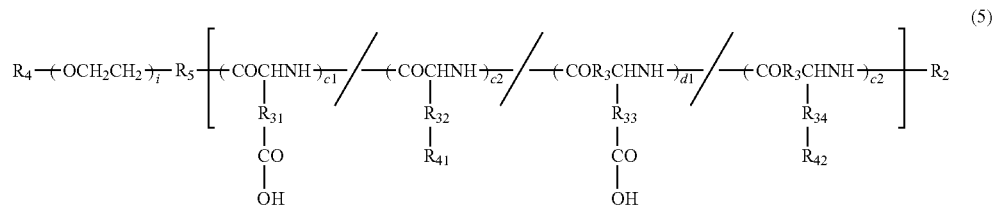

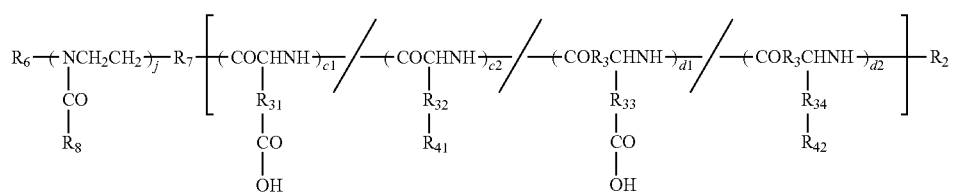

wherein: $R_2$ represents a hydrogen atom, an acetyl group, a trifluoroacetyl group, an acryloyl group or a methacryloyl group;

$R_3$s each independently represent a methylene group or an ethylene group;

$R_{31}$ and $R_{32}$ each independently represent a methylene group or an ethylene group;

$R_{33}$ and $R_{34}$ each independently represent a single bond, or a methylene group or an ethylene group;

$R_{41}$ and $R_{42}$ each independently represent a benzyloxycarbonyl group, a thiol group, a $C_{1-12}$ alkyl group including a thiol group, —$SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —$CONH(CH_2)_s$—$X_3$, wherein s is an integer from 0 to 20, and $X_3$ is a thiol group, a $C_{1-12}$ alkyl group including a thiol group or —$SR_{30}$ ($R_{30}$ is the same as above);

$R_4$ represents a hydrogen atom or an optionally substituted linear or branched $C_{1-12}$ alkyl group;

$R_5$ represents —$(CH_2)_g NH$— and g is an integer from 0 to 5;

$R_6$ and $R_7$ are respectively the same as $R_4$ and $R_5$;

$R_8$ represents a linear or branched $C_{1-12}$ alkyl group;

c1 and c2 are an integer from 0 to 5,000, d1 and d2 are an integer from 0 to 5,000, and c1+c2+d1+d2 is 2 to 5,000;

i and j are an integer from 5 to 2,500; and

"/" means that the sequence order of monomer units is arbitrary.

Preferably, in the above-described formula (5) or (6):

$R_2$ represents a hydrogen atom;

$R_3$ represents a methylene group;

$R_{31}$, $R_{32}$, $R_{33}$ and $R_{34}$ represent a methylene group;

$R_4$ represents a methyl group;

$R_6$ represents a methyl group;

$R_8$ represents —$CH(CH_3)_2$;

c1 and c2 are an integer from 0 to 200, d1 and d2 are an integer from 0 to 200, and c1+c2+d1+d2 is 10 to 200;

i is an integer from 10 to 300; and j is an integer from 10 to 300.

More preferably, in the above-described formula (5) or (6):

$R_2$ represents a hydrogen atom;

$R_3$ represents a methylene group;

$R_{31}$, $R_{32}$, $R_{33}$ and $R_{34}$ represent a methylene group;

$R_{41}$ and $R_{42}$ represent a thiol group;

$R_4$ represents a methyl group;

$R_6$ represents a methyl group;

$R_8$ represents —$CH(CH_3)_2$;

c1 and c2 are an integer from 0 to 200, d1 and d2 are an integer from 0 to 200, and c1+c2+d1+d2 is 10 to 200;

i is an integer from 10 to 300; and j is an integer from 10 to 300.

Further, examples of the present invention include those in which the block copolymer (I) is represented by the formula (3) and the block copolymer (II) is represented by the formula (5).

In one embodiment of the present invention, a vesicle encapsulates a compound.

Advantageous Effect of Invention

According to the present invention, an electrostatically bonded vesicle is provided. In the vesicle of the present invention, a charged segment bears a thiol group or disulfide group, the inside and outside of a membrane is hydrophilic, a drug and the like can be encapsulated in the hollow in the membrane, and a bond between a cationic segment and an anionic segment can be controlled. Moreover, it is possible to control vesicle degradation induction and release property based on spontaneous crosslinking in the formed electrostatically bonded-type membrane based on the disulfide formation between thiol groups and responsiveness of the disulfide bond to a reducing environment, an oxidizing environment or an environment in which radical generation may occur. Therefore, the vesicle of the present invention is very useful on the point that it can be applied for the drug delivery system (DDS).

DESCRIPTION OF EMBODIMENTS

Figure 1:
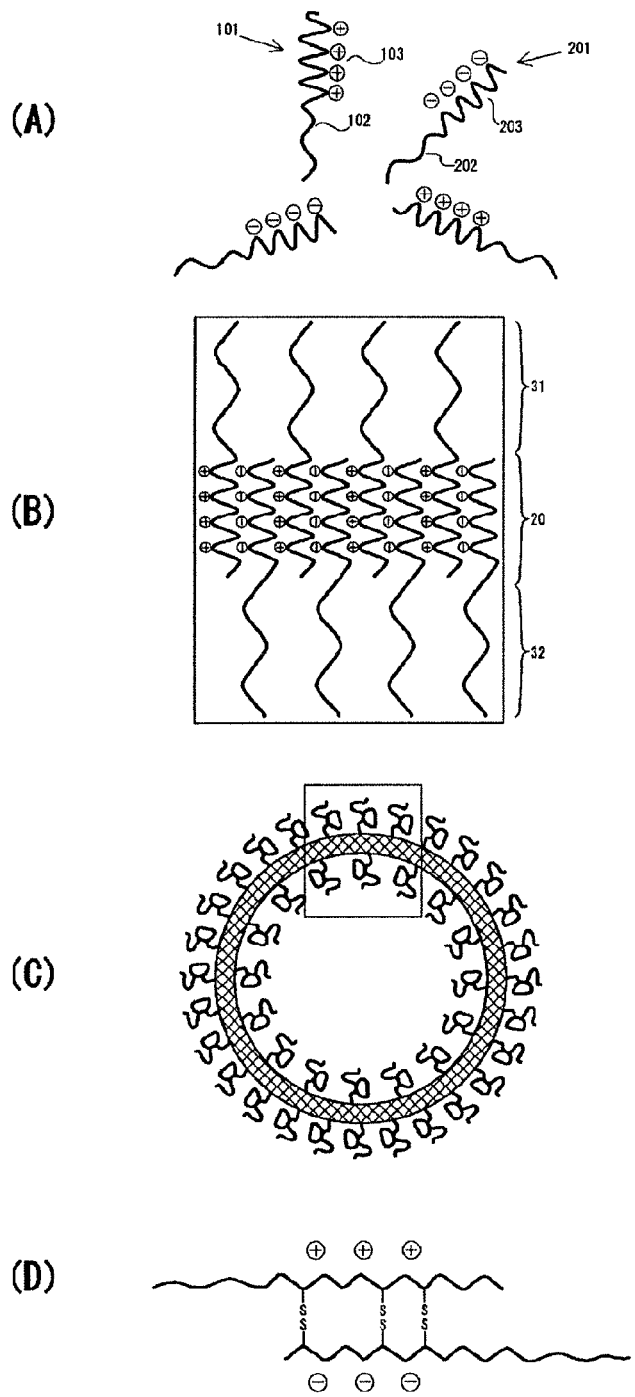
FIG. 1 is an exemplary view showing a structure of a vesicle and a mechanism of formation of the vesicle.

Hereinafter, the present invention will be described in detail.

1 Summary

The present inventors found that a novel vesicle having excellent structure stability and environmental responsiveness can be obtained by using two polymers including a positively-charged segment and a negatively-charged segment and further crosslinking these segments. The present inventors also found that a novel vesicle can be easily produced by mixing the above-described two polymers in an aqueous solution. The present invention was achieved based on these findings.

The vesicle of the present invention can be prepared without use of an organic solvent, and can be advantageously used in the biomaterial field and DDS. Further, the vesicle of the present invention has a space (hollow) inside the membrane, and a large amount of substance such as a compound can be encapsulated therein. Therefore, the vesicle of the present invention can be advantageously used, for example, as a delivery carrier for a substance in the body and a drug or fine reactor particles in which a hollow serves as a reaction field of an enzyme. Moreover, the structure of the vesicle of the present invention can be stably maintained in the presence of saline or serum, and it is possible to impart various functions such as semi permeability to the membrane of the vesicle. Furthermore, in the vesicle of the present invention, charged segments are crosslinked by a disulfide bond or the like, and the bond can be cleaved under reducing conditions. Therefore, the vesicle of the present invention can be advantageously used as a biomaterial or drug delivery system having excellent structure stability and environmental responsiveness.

The term "vesicle" as used herein means a basic structure which has a hollow and is closed by a membrane.

Unless otherwise specified, the term "alkyl" or "alkoxy" as used herein as a group or a part of the group means that the group is a linear, branched or cyclic alkyl or alkoxy. Further, for example, "$C_{1-12}$" of "$C_{1-12}$ alkyl group" means that the carbon number of the alkyl group is 1 to 12.

Examples of the "$C_{1-12}$ alkyl group" in the present invention include methyl group, ethyl group, n-propyl group, isopropyl group, n-butyl group, sec-butyl group, tert-butyl group, n-pentyl group, n-hexyl group, decyl group and undecyl group. Examples of the "$C_{1-6}$ alkyl group" include methyl group, ethyl group, n-propyl group, isopropyl group, n-butyl group, sec-butyl group, tert-butyl group, n-pentyl group and n-hexyl group.

Unless otherwise specified, the term "aryl" as used herein means phenyl, naphthyl, anthnyl, pyrenyl or the like.

The term "halogen atom" as used herein means fluorine atom, chlorine atom, bromine atom or iodine atom.

The expression that the alkyl group is "optionally substituted" as used herein means that one or more hydrogen atoms on the alkyl group may be substituted with one or more substituents (which may be the same or different). It is apparent to those skilled in the art that the maximum number of substituents can be determined depending on the number of substitutable hydrogen atoms on the alkyl. Regarding groups other than the alkyl group, the expression "optionally substituted" is interpreted in the same way.

Substituents as used herein are selected from the group consisting of halogen atom, aryl group, hydroxyl group, amino group, carboxyl group, cyano group, formyl group, dimethylacetalized formyl group, diethylacetalized formyl group, $C_{1-6}$ alkoxycarbonyl group, $C_{2-7}$ acylamide group, tri-$C_{1-6}$ alkylsiloxy group (wherein $C_{1-6}$ alkyls may be the same or different), siloxy group and silylamino group.

2. Vesicle

One feature of the vesicle of the present invention is that it includes a membrane formed by the interaction of water-soluble and charged polymers.

The vesicle of the present invention has a membrane which is formed from a first polymer and a second polymer described below (with the proviso that a combination of (b) and (d) is excepted). In the membrane, the cationic segment and anionic segment of the polymers are partially crosslinked.

First Polymer:
(a) a block copolymer (I) having both an electrically non-charged hydrophilic segment and a cationic segment
(b) an amino acid polymer (I) having a cationic segment Second Polymer:
(c) a block copolymer (II) having both an electrically non-charged hydrophilic segment and an anionic segment
(d) an amino acid polymer (II) having an anionic segment In this regard, the outside and inside of the membrane of the present invention is preferably hydrophilic, and a combination of the above-described amino acid polymers (b) and (d) is excluded.

FIG. 1 is a schematic view showing, as one embodiment, a structure of the vesicle of the present invention and a mechanism of formation of the vesicle. In FIG. 1, for convenience, as the first and second polymers, block copolymers, each of which consists of an electrically non-charged hydrophilic segment and a charged segment (a combination of (a) and (c) above), are illustrated.

In FIG. 1A, a first block copolymer 101 has an electrically non-charged hydrophilic segment 102 and a positively-charged charged segment (cationic segment) 103, and a second block copolymer 201 has an electrically non-charged hydrophilic segment 202 and a negatively-charged charged segment (anionic segment) 203. Further, the first block copolymer 101 and the second block copolymer 201 are self-assembled when put into a system in which the charge interaction may occur, and as shown in FIG. 1B, an intermediate layer 20 of an ion complex made of the charged segments 103 and 203, and two hydrophilic layers made of the electrically non-charged hydrophilic segments 102 and 202 (outer layer 31 and inner layer 32) are formed, and a vesicle (C) having the structure (B) as a membrane is produced. Note that FIG. 1B is an enlarged view schematically showing the portion within the frame in FIG. 1C.

Further, a side chain of the charged segment has a thiol group or the like, and for example, a disulfide bond can be formed under oxidation conditions (FIG. 1D).

Examples of oxidation conditions include air oxidation as well as general methods using, as an oxidant, iodine, hydrogen peroxide, potassium permanganate, copper sulfate, lead dioxide, $Fe^{3+}$ complex, nitrogen oxide such as NO, $N_2O_4$ and $NO_2$, dimethylsulfoxide or the like.

As described above, the formation of the vesicle of the present invention is driven mainly by the electrostatic interaction between the charged segments and crosslinking such as the disulfide bond. Therefore, it is possible to control the formation/cleavage of the vesicle and permeability of the membrane by the ionic strength, pH change and oxidation-reduction reaction in the body. As a result, the vesicle of the present invention can indicate excellent environmental responsiveness.

Further, as shown in FIG. 1C, the membrane of the vesicle has a three-layer structure consisting of the outer layer 31, intermediate layer 20 and inner layer 32.

Since the vesicle of the present invention has the inner layer composed of the electrically non-charged hydrophilic segment, the central void thereof may contain an aqueous medium.

The form of the vesicle of the present invention is usually a spherical shape. The particle diameter of the vesicle of the present invention is not particularly limited as long as the vesicle has a hollow structure, but preferably 10 μm or less, and more preferably 50 nm to 1 μm.

The vesicle of the present invention is a vesicle in which a polyion complex (PIC) is formed in the intermediate layer. Therefore, the vesicle of the present invention may be sometimes referred to as "PICsome".

3. Segment

Hereinafter, segments which constitute the vesicle of the present invention will be described.

(1) Charged Segment

The charged segment included in the first polymer and the charged segment included in the second polymer can be charged with mutually opposite electric charges. In the present invention, the charged segment included in the first polymer is a cationic segment, and the charged segment included in the second polymer is an anionic segment.

Further, in the present invention, when polyamine is used as the cationic segment, the polyamine can be positively charged by acid addition thereto. The type of acid to be added is appropriately determined according to use of the vesicle, etc.

According to a preferred embodiment of the present invention, the cationic segment of the first polymer is represented by the following formula (1):

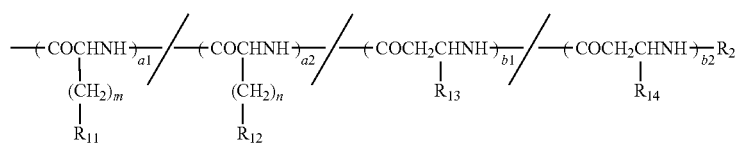

(1)

In the formula (1) above, $R_2$ represents a hydrogen atom, an acetyl group, a trifluoroacetyl group, an acryloyl group or a methacryloyl group.

Further, $R_{11}$ and $R_{13}$ each independently represent $-(CH_2)_3NH_2$ or $-CONH(CH_2)_s-X_1$, wherein: s is an integer from 0 to 20; and $X_1$ is at least one selected from the group consisting of $-NH_2$, a pyridyl group, a morpholyl group, a 1-imidazolyl group, a piperazinyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group, a piperidinyl group, a guanidino group, a diisopropylamino group, a dimethylamino group, a diethylamino group, $-(CH_2)_tNH_2$ and $-(NR_9(CH_2)_o)_pNHR_{10}$, wherein: $R_9$ represents a hydrogen atom or a methyl group; $R_{10}$ represents a hydrogen atom, an acetyl group, a trifluoroacetyl group, a benzyloxycarbonyl group, $-C(=NH)-NH_2$ or a tert-butoxycarbonyl group; o is an integer from 1 to 15; p is an integer from 1 to 5; and t is an integer from 0 to 15.

$R_{12}$ and $R_{14}$ each independently represent a thiol group, a $C_{1-12}$ alkyl group including a thiol group, $-SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or $-CONH(CH_2)_s-X_2$, wherein: s is an integer from 0 to 20; and $X_2$ is at least one selected from the group consisting of a thiol group, a $C_{1-12}$ alkyl group including a thiol group, $SR_{30}$ ($R_{30}$ is the same as above), and a pyridyl group, a 1-imidazolyl group, a piperazinyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group and a piperidinyl group, which are substituted with a thiol group, a $C_{1-12}$ alkyl group including a thiol group or $SR_{30}$ ($R_{30}$ is the same as above), and $-S-S-$ $(CH_2)_tNH_2$, $-S-S-(NR_9(CH_2)_o)_pNHR_{10}$, $-(CH_2)_t$ $NHCO(CH_2)_uSH$ and $-(CH_2)_tNHC(=NH)(CH_2)_vSH$, wherein $R_9$, $R_{10}$, o, p and t are the same as above, u is an integer from 0 to 15, and v is an integer from 0 to 15, and m and n are 1 or 2.

Examples of the $C_{1-12}$ alkyl group including a thiol group include mercaptomethyl group, 2-mercapto ethyl group, 3-mercaptopropyl group, 3-mercapto butyl group, 4-mercaptobutyl group, 6-mercaptohexyl group, 3-mercaptohexyl group, 8-mercaptooctyl group and 12-mercaptododecyl group.

a1 and a2 are an integer from 0 to 5,000, b1 and b2 are an integer from 0 to 5,000, and a1+a2+b1+b2 is 2 to 5,000.

Further, "/" means that the sequence order of monomer units is arbitrary.

In this regard, the thiol group may be protected with a protective group. $R_{30}$ is a protective group of the thiol group, and examples thereof include benzyl group, 4-methoxybenzyl group, 4-methylbenzyl group, N-(acetyl)aminomethyl group, tert-butyl group, trityl group, 2-pyridinesulfenyl group and 3-nitro-2-pyridinesulfenyl group.

In the formula (1) above, when $R_{11}$ and $R_{13}$ represent $-CONH(CH_2)_s-X_1$, $X_1$ may be the same or different functional group for every repeating unit of the charged segment.

According to a more preferred embodiment of the present invention, in the formula (1) above: $R_{11}$ and $R_{13}$ are each independently $-CONH(CH_2)_s-NH_2$ (s is an integer from 2 to 8); $R_{12}$ and $R_{14}$ are each independently a thiol group, $-CONH(C_{1-2})_s-S-S-(C_{1-2})_tNH_2$, $-CONH(CH_2)_s-SH$, $-CONH(CH_2)_sNHCO(CH_2)_uSH$ or $-CONH(CH_2)_sNHC(=NH)(CH_2)_vSH$ (s is an integer from 2 to 8, t is an integer from 0 to 15, u is an integer from 1 to 8, and v is an integer from 1 to 8); $R_2$ is a hydrogen atom; a1 and a2 are an integer from 0 to 200, b1 and b2 are an integer from 0 to 200, and a1+a2+b1+b2 is 10 to 200.

In this regard, in order to form a cross-linked structure including a disulfide bond, etc. between the cationic segment and the anionic segment, it is required that (i) the cationic segment and the anionic segment include a thiol group or a group obtained by sulfenylating a thiol group or the like, or that (ii) the cationic segment includes a disulfide bond. Therefore, in the case of crosslinking using the embodiment (i) above, it is preferred that at least one of a2 and b2 in the formula (1) is not 0.

In order to crosslink the segments, a linker can be used. The type of the linker for crosslinking the segments is not particularly limited, and it is sufficient when a disulfide bond is formed at both the ends of the linker and particles are stabilized. Examples of cross-linking agents for introducing the linker include alkyldithiol, thiosulfinate (e.g., 1,2-dithiane-t-4,t-5-diol r-1-oxide) and a sulfenylating agent synthesized from alkyldithiol.

In the case of crosslinking using the embodiment (ii) above, in the presence of a suitable condensation agent, an amide bond is formed between an amino group of the terminus of the side chain of the cationic segment and a carboxyl group of the terminus of the side chain of the anionic segment, thereby crosslinking the segments.

When using a crosslinking agent, the type of the crosslinking agent is not limited, and can be suitably selected depending on the intended use of the vesicle, the types of the first polymer and the second polymer, the types of other components of the membrane, etc. However, in terms of efficient crosslinking and enhancement of stability of a substance-encapsulated vesicle, it is preferred to use a crosslinking agent, which reacts with a charged group had by a charged segment of the first polymer and the second polymer (for example, a cationic group such as an amino group, or an anionic group such as a carboxyl group) and does not react with any encapsulated substance. Specific examples of the crosslinking agent include: a crosslinking agent for crosslinking an amino group (e.g., glutaraldehyde, dimethyl suberimidate dihydrochloride (DMS), dimethyl 3,3'-dithiobispropionimidate (DTBP)); a crosslinking agent for providing a crosslink by condensation of an amino group and a carboxyl group (e.g., 1-ethyl-3-(3-dimethylaminopropyl)carbodiimide (EDC)); and a crosslinking agent for crosslinking a phosphate group (e.g., a metal ion such as a calcium ion), and glutaraldehyde, EDC, etc. are preferred, and EDC is particularly preferred. One type of crosslinking agent may be used solely. Alternatively, 2 or more types of crosslinking agents may be used in any combination at any ratio.

When using the crosslinking agent, the amount thereof can be suitably set by those skilled in the art depending on properties of the crosslinking agent, properties of groups to be crosslinked or the like. For example, in the case of a crosslinking agent which provides crosslinking by condensation of an amino group and a carboxyl group, the crosslinking agent can be used in an amount of 0.05 to 20 equivalents, preferably 0.1 to 20 equivalents, and for example, 0.1, 0.5, 1.0, 5.0 or 10 equivalents of the carboxyl group or amino group. Further, in the case of crosslinking using thiosulfinate or the like, it can be used in an amount of 0.05 to 20 equivalents, and preferably 0.1 to 10 equivalents of a thiol group at the carboxyl group side or amino group side.

In the present invention, when the first polymer forms an amino acid polymer (I) having a cationic segment, the cationic segment may be represented by the formula (1) above, and examples of the terminus opposite to $R_2$ thereof include —NH($CH_2$)$_{k-1}$$CH_3$ and —NH—($CH_2$)$_{k-1}$—C(triple bond)CH (k is an integer of 1 or more), and —NH($CH_2$)$_3$$CH_3$ is preferred.

In one embodiment of the present invention, the above-described amino acid polymer (1) is made of the cationic segment.

According to a preferred embodiment of the present invention, the anionic segment of the second polymer is represented by the following formula (2):

Further, $R_{31}$ and $R_{32}$ each independently represent a methylene group or an ethylene group, and $R_{33}$ and $R_{34}$ each independently represent a single bond, or a methylene group or an ethylene group.

$R_{41}$ and $R_{42}$ each independently represent a benzyloxycarbonyl group, a thiol group, a $C_{1-12}$ alkyl group including a thiol group, —$SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —CONH($CH_2$)$_s$—$X_3$, wherein s is an integer from 0 to 20, and $X_3$ is a thiol group, a $C_{1-12}$ alkyl group including a thiol group or —$SR_{30}$ ($R_{30}$ is the same as above).

c1 and c2 are an integer from 0 to 5,000, d1 and d2 are an integer from 0 to 5,000, and c1+c2+d1+d2 is 2 to 5,000; and "/" means that the sequence order of monomer units is arbitrary.

In the formula (2) above, $R_3$ may be the same or different functional group for every repeating unit of the charged segment.

According to a more preferred embodiment of the present invention, in the formula (2) above: $R_2$ represents a hydrogen atom; $R_3$ represents a methylene group; $R_{31}$, $R_{32}$, $R_{33}$ and $R_{34}$ represent a methylene group; $R_{41}$ and $R_{42}$ are a thiol group or —CONH($CH_2$)$_s$—SH (S is an integer from 2 to 8); and c1 and c2 are an integer from 0 to 200, d1 and d2 are an integer from 0 to 200, and c1+c2+d1+d2 is 10 to 200.

Further, as described above, when a thiol group or a group obtained by sulfenylating a thiol group or the like is introduced into the cationic segment and the anionic segment, a disulfide bond can be formed between the segments. Therefore, when introducing a thiol group or a group obtained by sulfenylating a thiol group or the like into the cationic segment, it is preferred to allow a disulfide bond to be formed with the anionic segment. Accordingly, in this case, in order to introduce a thiol group into the side chain of the anionic segment, it is preferred that at least one of c2 and d2 in the formula (2) is not 0, and it is more preferred that at least one of c1 and d1 and at least one of c2 and d2 are not 0.

Further, as described above, when a disulfide bond is included in the side chain of the cationic segment, both c2 and d2 in the formula (2) may be 0. Further, an amide bond is formed between an amino group of the terminus of the side chain of the cationic segment and a carboxyl group of the terminus of the side chain of the anionic segment, thereby crosslinking the segments.

The type of the crosslinking agent and the combination are the same as above.

In the present invention, when the second polymer forms an amino acid polymer (II) having an anionic segment, the anionic segment may be represented by the formula (2)

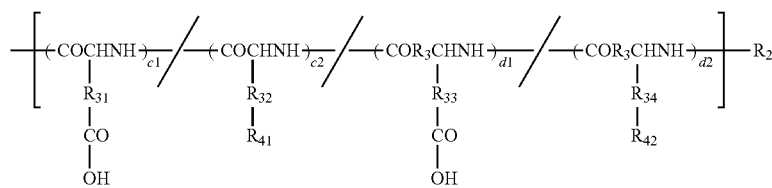

(2)

In the formula (2) above: $R_2$ represents a hydrogen atom, an acetyl group, a trifluoroacetyl group, an acryloyl group or a methacryloyl group; and $R_3$s each independently represent a methylene group or an ethylene group.

above, and examples of the terminus opposite to $R_2$ thereof include —NH($CH_2$)$_{w-1}$$CH_3$ and —NH—($CH_2$)$_{w-1}$—C(triple bond)CH (w is an integer of 1 or more), and —NH($CH_2$)$_3$$CH_3$ is preferred.

In one embodiment of the present invention, the above-described amino acid polymer (II) is made of the anionic segment.

(2) Electrically Non-Charged Hydrophilic Segment

The electrically non-charged hydrophilic segment is a polymer segment which is uncharged and hydrophilic. The term "electrically non-charged" as used herein means that the entire segment is neutral. Examples thereof include a case wherein the segment does not have any positive or negative charge. Further, even if the segment has a positive/negative charge within its molecule, when a local effective charge density is not high and the charge of the entire segment is neutralized to the extent that it does not prevent the formation of the vesicle by self-assembly, it also corresponds to "electrically non-charged". The term "hydrophilic" means that solubility is shown with respect to an aqueous medium.

Examples of the electrically non-charged hydrophilic segment to be included in the block copolymer include polyalkylene glycol such as polyethylene glycol, and poly(2-oxazoline) such as poly(2-methyl-2-oxazoline), poly(2-ethyl-2-oxazoline), poly(2-n-propyl-2-oxazoline) and poly(2-isopropyl-2-oxazoline). Examples thereof further include polysaccharide, polyvinyl alcohol, polyvinylpyrrolidone, polyacrylamide, polymethacrylamide, polyacrylic acid ester, polymethacrylic acid ester, poly(2-methacryloyloxyethylphosphorylcholine), a peptide with an isoelectric point of about 7, a protein and derivatives thereof. When the above-described electrically non-charged hydrophilic segment is included, the block copolymer can exist stably in an aqueous solution without assembly/precipitation, thereby efficiently constructing the vesicle. Moreover, when the vesicle is constructed with the block copolymers including the above-described electrically non-charged hydrophilic segment, the vesicle can maintain its structure stably in an aqueous solution.

According to a preferred embodiment of the present invention, the electrically non-charged hydrophilic segment of the first and second polymers is polyethylene glycol and/or poly(2-isopropyl-2-oxazoline), and preferably polyethylene glycol. Use of polyethylene glycol as the electrically non-charged hydrophilic segment is advantageous when biocompatibility is imparted to the vesicle.

When using polyethylene glycol as the electrically non-charged hydrophilic segment, the molecular weight of polyethylene glycol is preferably 500 to 15,000, and more preferably 1,000 to 5,000. Use of an electrically non-charged hydrophilic segment having the above-described molecular weight for the block copolymer is advantageous when the vesicle is formed in preference to a micelle.

4. Block Copolymer (1) Block Copolymer (I) Having Cationic Segment

According to a preferred embodiment of the present invention, the block copolymer (I) having a cationic segment is represented by the following formula (3) or (4):

In the formulae:

$R_2$ represents a hydrogen atom, an acetyl group, a trifluoroacetyl group, an acryloyl group or a methacryloyl group;

$R_{11}$ and $R_{13}$ each independently represent —$(CH_2)_3NH_2$ or —$CONH(CH_2)_s$—$X_1$, wherein: s is an integer from 0 to 20; and $X_1$ is at least one selected from the group consisting of —$NH_2$, a pyridyl group, a morpholyl group, a 1-imidazolyl group, a piperazinyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group, a piperidinyl group, a guanidino group, a diisopropylamino group, a dimethylamino group, a diethylamino group, —$(CH_2)_tNH_2$ and —$(NR_9(CH_2)_o)_pNHR_{10}$, wherein: $R_9$ represents a hydrogen atom or a methyl group; $R_{10}$ represents a hydrogen atom, an acetyl group, a trifluoroacetyl group, a benzyloxycarbonyl group, —$C(=NH)$—$NH_2$ or a tert-butoxycarbonyl group; o is an integer from 1 to 15; p is an integer from 1 to 5; and t is an integer from 0 to 15.

$R_{12}$ and $R_{14}$ each independently represent a thiol group, a $C_{1-12}$ alkyl group including a thiol group, —$SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —$CONH(CH_2)_s$—$X_2$, wherein: s is an integer from 0 to 20; and $X_2$ is at least one selected from the group consisting of a thiol group, a $C_{1-12}$ alkyl group including a thiol group, $SR_{30}$ ($R_{30}$ is the same as above), and a pyridyl group, a 1-imidazolyl group, a piperazinyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group and a piperidinyl group, which are substituted with a thiol group, a $C_{1-12}$ alkyl group including a thiol group or $SR_{30}$ ($R_{30}$ is the same as above), and —S—S—$(CH_2)NH_2$, —S—S—$(NR_9(CH_2)_o)_pNHR_{10}$, —$(CH_2)_tNHCO(CH_2)_uSH$ and —$(CH_2)_tNHC(=NH)(CH_2)_vSH$, wherein $R_9$, $R_{10}$, o, p and t are the same as above, u is an integer from 0 to 15, and v is an integer from 0 to 15;

m and n are 1 or 2;

$R_4$ represents a hydrogen atom or an optionally substituted linear or branched $C_{1-12}$ alkyl group;

$R_5$ represents —$(CH_2)_gNH$— and g is 0 to 5;

$R_6$ and $R_7$ are respectively the same as $R_4$ and $R_5$;

$R_8$ represents a linear or branched $C_{1-12}$ alkyl group;

a1 and a2 are an integer from 0 to 5,000, b1 and b2 are an integer from 0 to 5,000, and a1+a2+b1+b2 is 2 to 5,000;

e is an integer from 5 to 2,500, and f is an integer from 5 to 2,500; and

"/" means that the sequence order of monomer units is arbitrary.

In the formulae (3) and (4) above, when $R_{11}$ and $R_{13}$ represent —$CONH(CH_2)_s$—$X_1$, $X_1$ may be the same or different functional group for every repeating unit of the block copolymer.

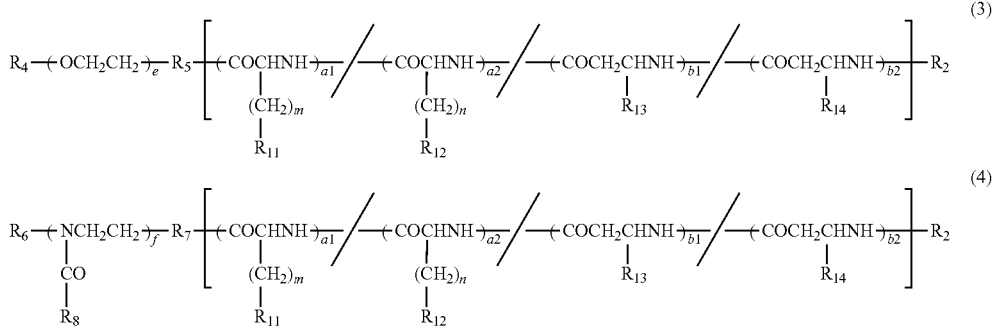

According to a more preferred embodiment of the present invention, in the formulae (3) and (4) above: $R_{11}$ and $R_{13}$ are each independently —CONH(CH$_2$)$_s$—NH$_2$ (s is an integer from 2 to 8); $R_{12}$ and $R_{14}$ are each independently a thiol group, —CONH(CH$_2$)$_s$—S—S—(CH$_2$)$_t$NH$_2$, —CONH(CH$_2$)$_s$—SH, —CONH(CH$_2$)$_s$NHCO(CH$_2$)$_u$SH or —CONH(CH$_2$)$_s$NHC(=NH)(CH$_2$)$_v$SH (s is an integer from 2 to 8, t is an integer from 0 to 15, u is an integer from 1 to 8, and v is an integer from 1 to 8); $R_2$ is a hydrogen atom; $R_4$ is a methyl group; a1 and a2 are an integer from 0 to 200, b1 and b2 are an integer from 0 to 200, and a1+a2+b1+b2 is 10 to 200, e is an integer from 10 to 300, and f is an integer from 10 to 300.

(2) Block Copolymer (II) Having Anionic Segment

According to a preferred embodiment of the present invention, the block copolymer (II) having an anionic segment is represented by the following formula (5) or (6):

According to another more preferred embodiment of the present invention, in the formulae (5) and (6) above: $R_2$ is a hydrogen atom; $R_3$ is a methylene group; $R_{31}$, $R_{32}$, $R_{33}$ and $R_{34}$ are a methylene group; $R_4$ is a methyl group; $R_6$ is a methyl group; $R_8$ is —CH(CH$_3$)$_2$; c1 and c2 are an integer from 0 to 200, d1 and d2 are an integer from 0 to 200, and c1+c2+d1+d2 is 10 to 200; i is an integer from 10 to 300; and j is an integer from 10 to 300.

According to another more preferred embodiment of the present invention, in the formulae (5) and (6) above: $R_2$ is a hydrogen atom; $R_3$ is a methylene group; $R_{31}$, $R_{32}$, $R_{33}$ and $R_{34}$ are a methylene group; $R_{41}$ and $R_{42}$ represent a thiol group; $R_4$ is a methyl group; $R_6$ is a methyl group; $R_8$ is —CH(CH$_3$)$_2$; c1 and c2 are an integer from 0 to 200, d1 and

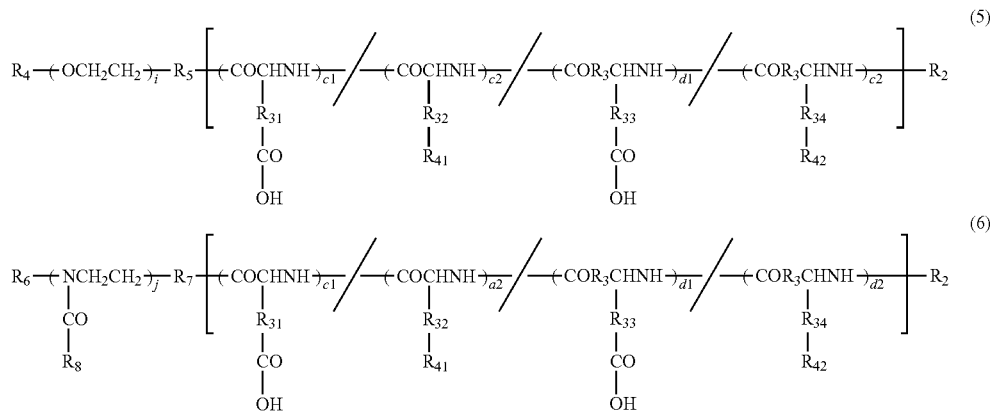

In the formulae:

$R_2$ represents a hydrogen atom, an acetyl group, a trifluoroacetyl group, an acryloyl group or a methacryloyl group;

$R_3$s each independently represent a methylene group or an ethylene group;

$R_{31}$ and $R_{32}$ each independently represent a methylene group or an ethylene group;

$R_{33}$ and $R_{34}$ each independently represent a single bond, or a methylene group or an ethylene group;

$R_{41}$ and $R_{42}$ each independently represent a benzyloxycarbonyl group, a thiol group, a $C_{1-12}$ alkyl group including a thiol group, —SR$_{30}$ (R$_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —CONH(CH$_2$)$_s$—X$_3$, wherein s is an integer from 0 to 20, and X$_3$ is a thiol group, a $C_{1-12}$ alkyl group including a thiol group or —SR$_{30}$ (R$_{30}$ is the same as above);

$R_4$ represents a hydrogen atom or an optionally substituted linear or branched $C_{1-12}$ alkyl group;

$R_5$ represents —(CH$_2$)$_g$NH— and g is an integer from 0 to 5;

$R_6$ and $R_7$ are respectively the same as $R_4$ and $R_5$;

$R_8$ represents a linear or branched $C_{1-12}$ alkyl group;

c1 and c2 are an integer from 0 to 5,000, d1 and d2 are an integer from 0 to 5,000, and c1+c2+d1+d2 is 2 to 5,000;

i and j are an integer from 5 to 2,500; and

"/" means that the sequence order of monomer units is arbitrary.

In the formulae (5) and (6) above, $R_3$ may be the same or different functional group for every repeating unit of the block copolymer.

d2 are an integer from 0 to 200, and c1+c2+d1+d2 is 10 to 200; i is an integer from 10 to 300; and j is an integer from 10 to 300.

5. Production of Vesicle

In the vesicle of the present invention, the hollow thereof may contain a substance such as a compound. Further, in the vesicle of the present invention, a substance such as a compound can be inserted in the membrane thereof. The above-described substance can be suitably selected depending on the intended use and properties of the vesicle, and examples thereof include a drug, protein, fluorescent dye, nucleic acid and particle.

Since the vesicle of the present invention is formed using the electrostatic interaction between charged segments and crosslinking, the vesicle can be easily produced by mixing the first polymer (I) and the second polymer (11) in an aqueous solution. Moreover, according to the production method of the present invention, the vesicle can be produced without organic solvent, and therefore, it can be advantageously used in the biomaterial field and DDS.

The ratio between the first charged segment and the second charged segment (the ratio between the cationic segment and the anionic segment) and the ratio between the electrically non-charged hydrophilic segment and the charged segment may be arbitrarily determined. However, in terms of promotion of self-assembly of the first polymer and the second polymer and efficient production of a homogeneous vesicle, the ratios are preferably selected based on the criteria described below.

Firstly, regarding the ratio between the cationic segment and the anionic segment, it is desired to be adjusted so that the C/A ratio defined as formula (1) below becomes usually 0.3, preferably 0.5 or more, and more preferably 0.6 or more, and becomes usually less than 3.0, preferably 2.0 or less, and more preferably 1.7 or less.

$$C/A \text{ ratio (molar ratio)} = \frac{[\text{Mole number of cationic group in first and second polymers}]}{[\text{Mole number of anionic group in first and second polymers}]} \quad \text{formula (i)}$$

In this regard, values of the mole numbers of the cationic group and the anionic group in the first and second polymers depend on the structures of the cationic segment and the anionic segment, and can be obtained by a general potentiometric (acid/base) titration method.

In the production of the present invention, firstly, a first aqueous solution containing the first polymer (I) and a second aqueous solution containing the second polymer (II) are prepared. In this regard, the first and second aqueous solutions may be purified by filtration if desired.

The ratio between the total charge number of the first polymer (I) in the first aqueous solution and the total charge number of the second polymer (II) in the second aqueous solution is preferably 5:1 to 1:5, and more preferably about 1:1. When the polymer is a block copolymer, the total charge number of the block copolymer is suitably determined by those skilled in the art depending on the number of repeating units constructing the charged segment in the block copolymer, the charge number of the repeating units, etc. Use of the two polymers at the above-described ratio is advantageous when efficiently producing a homogeneous vesicle.

Further, the concentration of the first polymer (I) in the first aqueous solution and the concentration of the second polymer (II) in the second aqueous solution are suitably determined in consideration of the above-described ratio between the total charge numbers of the polymers, solubility of the polymers in the aqueous solutions, the size of a vesicle to be prepared, efficiency of vesicle formation, etc.

Further, since a polymer having a hydrophilic segment is water-soluble, the solvent in the first and second aqueous solutions is preferably water or a buffer, and more preferred examples thereof include 10 mM Tris/HCl buffer, phosphate buffer and HEPES buffer.

Further, pHs of the first and second aqueous solutions may be suitably adjusted within a range in which formation of a vesicle is not prevented, and the pHs are preferably 5 to 9, and more preferably about 7. The pHs can be easily adjusted by using a buffer as the solvent in the aqueous solutions. Use of the first and second aqueous solutions with pHs thereof adjusted is advantageous when maintaining the charge state of the block copolymers and efficiently forming a vesicle.

The temperatures of the above-described first and second aqueous solutions are suitably determined depending on the solubility of the polymers in the solvents, and preferably 4 to 80° C., and more preferably 15 to 50° C.

The ionic strength of the above-described first and second aqueous solutions may be suitably adjusted within a range in which formation of a vesicle is not prevented, and is preferably 0 to 300 mM, and more preferably 0 to 150 mM.

Next, in the present invention, the first aqueous solution is mixed with the second aqueous solution. The mixing method is not particularly limited. The second aqueous solution may be added to the first aqueous solution, and the first aqueous solution may be added to the second aqueous solution. Alternatively, the first aqueous solution and the second aqueous solution may be simultaneously put into a container to be mixed. The mixture of the first aqueous solution and the second aqueous solution thus obtained may be suitably stirred.

The temperature of mixing the first aqueous solution and the second aqueous solution is not particularly limited if it is within a range in which formation of a vesicle is not prevented, but it is preferred that the temperature is set in view of the solubility of the polymers depending on the temperature. The temperature of mixing in this way is, for example, 15 to 50° C.

Further, in the production method of the present invention, the above-described mixture is allowed to stand to generate a vesicle in the mixture. After mixing, the formed vesicle may be immediately subjected to a desired application, but in order to equilibrate the system, the time to allow the mixture to stand may be set. The time to allow the mixture to stand varies depending on conditions such as efficiency of the vesicle formation, but is preferably 50 hours or less, and more preferably 30 hours or less. However, in the case where no crosslinking agent is used as described above, the diameter of the vesicle formed tends to increase over time, and therefore, there is a case where it is preferred not to set the time to allow the mixture to stand. The time to allow the mixture to stand varies depending on efficiency of the vesicle formation, but for example, since the system for generating a vesicle may be associated with particle growth, the time to be allowed to stand can be short. In this case, the time to be allowed to stand is 2 to 30 minutes. Further, in the case where sufficient equilibration of the system is intended, the time is 30 minutes or more, and preferably 30 to 50 hours.

By selecting standing for a short period of time (e.g., 2 to 30 minutes) or standing for a long period of time (e.g., 30 to 50 hours), the size of the vesicle obtained can be changed.

In the case of using a crosslinking agent, it may be added to the above-described mixture of the first and second aqueous solutions and then mixed. The crosslinking agent may be directly mixed, but it is also possible to prepare an aqueous solution containing the crosslinking agent and then mixed. At the time of preparation of the aqueous solution containing the crosslinking agent, preparation conditions such as an aqueous solvent, pH, temperature and ionic strength are the same as those for the first and second aqueous solutions described above.

In the present invention, by suitably adjusting the relationship between the amounts of the above-described first and second polymers and the amount of the condensation agent or crosslinking agent, the crosslinking ratio between charged segments can be changed to allow, for example, (i) control of the crosslinking ratio by the amount of the crosslinking agent to be added, and (ii) control of the membrane structure after crosslinking by adjustment of the chemical structure of the crosslinking agent. For example, by providing dense crosslinking, it is expected that permeability of the membrane can be decreased, and it is expected that stability of the vesicle can be increased, or that the response time can be extended. Alternatively, by using a crosslinking agent having a long alkyl chain or oligoethyleneoxide chain, it is expected that hydrophobicity, hydrophilicity and flexibility of the membrane can be controlled.

Further, when a substance such as a compound is to be encapsulated in the vesicle of the present invention, for example, by adding the substance to a mixed solution containing the first and second polymers during the vesicle formation, the substance can be encapsulated in the vesicle. Alternatively, it is also possible to add the substance to one or both of the first and second aqueous solutions in advance, and to prepare a mixed solution thereof, thereby encapsulating the substance in the vesicle. Therefore, the production method of the present invention preferably includes a step of adding a substance such as a compound to be encapsulated in the vesicle. At the time of encapsulating the substance in the vesicle, operational processes such as dialysis, dilution, condensation and stirring may be further added in a suitable manner. The same technique as above can also be used at the time of inserting the substance into the membrane of the vesicle.

Figure 4:
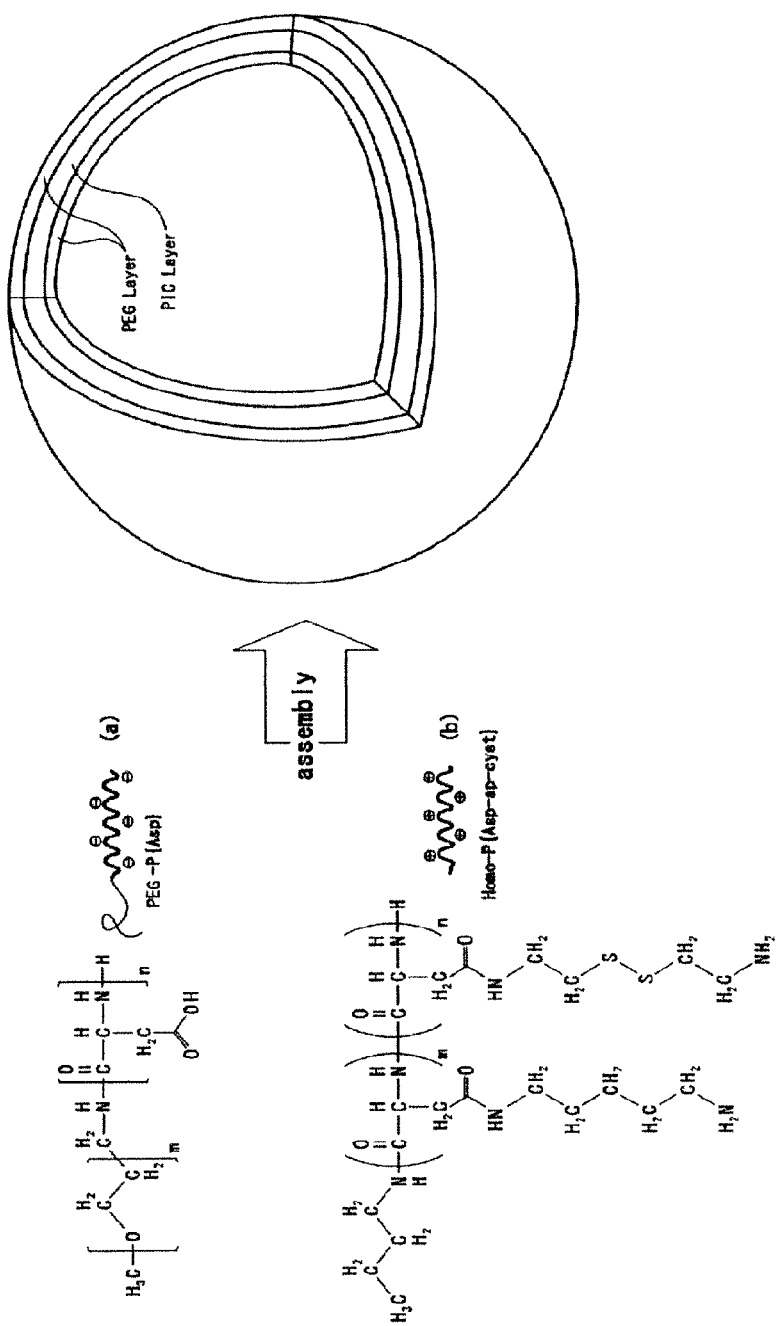
FIG. 4 is an exemplary schematic view of preparation scheme of the vesicle (PICsome) of the present invention.

An example of a preferred polymer for production of the vesicle of the present invention is shown in FIG. 4.

Hereinafter, the present invention will be more specifically described by way of examples. However, the present invention is not limited to these examples.

EXAMPLE 1

Production of Vesicle 1
<Materials>

1-Ethyl-3-(3-dimethylaminopropyl) carbodiimide hydrochloride (EDC), Dithiothreitol (DTT) and N-methyl-2-pyrrolidone (NMP) were purchased from Wako Pure Chemical Industries, Ltd. (Osaka). 1,5-diaminopentane (DAP) was purchased from Tokyo Chemical Industry Co., Ltd. (Tokyo). 2-2'-Dithiobis(ethylamine) (Cystamine) dihydrochloride was purchased from Sigma (St. Louis, Colo., USA). Cy3-monoreactive dye pack and PD-10 Desalting Column were purchased from GE Healthcare.

Regarding Cystamine free base (Cyst), after extraction, distillation was performed under reduced pressure, and then it was used. NMP was subjected to distillation under reduced pressure and then it was used. An anionic block copolymer PEG-poly(a,b-aspartic acid) (PEG-P(Asp); $M_n$ of PEG=2, 000, DP (Degree of Polymerization) of P(Asp)=75 or 85), fluorescently-labeled anionic block copolymer PEG-P(Asp)-Cy3, poly(β-benzyl L-aspartate) (homo-PBLA), and poly([5-aminopentyl]-a,b-aspartamide) (homo-P(Asp-AP); DP of P(Asp-AP)=82) were synthesized according to the method described in Anraku Y. et al., J. Am. Chem. Soc., 2010, 132 (5), 1631-1636.

<Synthesis of Cationic Amino Acid Polymer Having Disulfide Side Chain>

A lyophilized homo-PBLA (DP=72, 50 mg) was dissolved in 2.5 mL of NMP, and subsequently DAP (2 to 25 equivalents of PBLA) and 2-2'-Dithiobis(ethylamine)(Cyst) (25 to 40 equivalents of PBLA) were added to the solution, and the mixture was vigorously stirred at 5° C. for 1 hour. The reaction mixture was neutralized with 20 wt % acetic acid at 0 to 5° C., and it was dialyzed against 0.01 M hydrochloric acid for 3 days and subsequently against pure water for 3 days using a dialysis membrane having a molecular weight cutoff of 3,500.

The obtained solution was filtrated and lyophilized, thereby obtaining disulfide-containing polycationic homo-P (Asp-AP-Cyst). Note that "homo-P(Asp-AP-Cyst)" is apparently a random copolymer, but because homo-PBLA was used as a raw material, the description above is used herein. Other polymers (e.g., homo-P(Asp-AP)) may be described in the same way.

Figure 2:
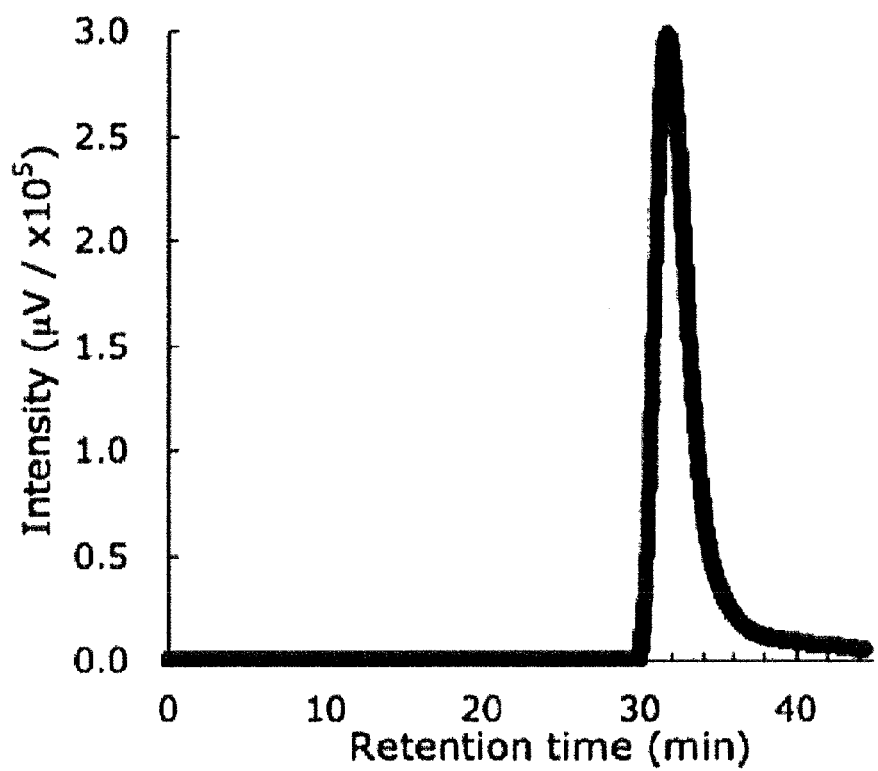
FIG. 2 shows the result of size exclusion chromatography of homo-P(Asp-AP-Cyst).

Using size exclusion chromatography, a monomodal peak was confirmed, and appropriate reaction progress was confirmed (FIG. 2).

Regarding the ratio of introduction of DAP and Cyst into the final product, the feed ratio was adjusted within the range from 1:1 to 1:20. According to $^1$H NMR spectrum, it became clear that it is possible to synthesize polycations with different Cyst contents (20 to 75% relative to the number of residues of the side chain).

Figure 3:
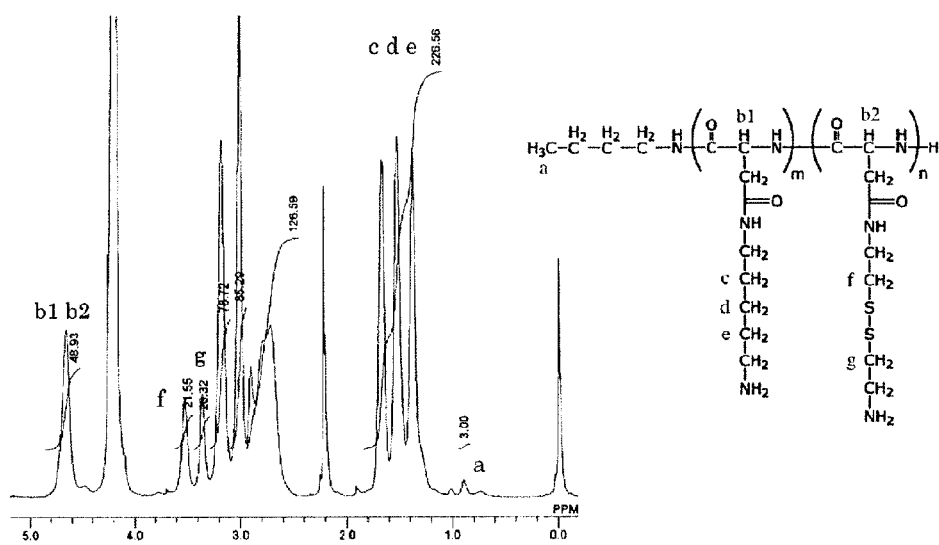
FIG. 3 shows the result of $^1H$ NMR measurement.

Hereinafter, a polymer obtained is described as homo-P $(Asp-AP_x-Cyst_y)_n$ (x+y=1, n is a total polymerization degree of cation chain). FIGS. 2 and 3 show results of analysis of homo-P(Asp-$AP_{0.8}$-$Cyst_{0.2}$)$_{48}$, which is a polymer containing 20% Cyst.

FIG. 2 shows the result of size exclusion chromatography (SEC) of homo-P(Asp-AP-Cyst).

Using Superdex 200 10/300 GL column (GE Healthcare) as a column, analysis was conducted using 10 mM phosphate buffer as an eluent (500 mM NaCl, pH 7.4) with a flow rate of 0.5 mL/min at 25° C. For chromatography, a system manufactured by JASCO Corporation was used.

FIG. 3 shows the result of $^1$H NMR measurement. In FIG. 3, it is confirmed that 38 units of DAP (peaks c-e; 6H) and 10 units of Cyst (peak f, g; 4H) were introduced, and it is confirmed that about 20% Cyst was introduced with respect to the 48-mer of the cationic side chain. Combined with the result in FIG. 2, it was identified as homo-P(Asp-$AP_{0.8}$-$Cyst_{0.2}$)$_{48}$, which is a polymer containing 20% Cyst. For the measurement, JNM-AL 300 (JEOL, Japan) was used, and the measurement was conducted in heavy water at 80° C. Note that in FIG. 3, "m" and "n" in copolymer represent the polymerization number (m=38, n=10).

<Preparation of Disulfide-Containing Vesicle (PICsome)>

10 mM phosphate buffer (0 mM NaCl, pH 7.4) solution of PEG-P(Asp)$_{85}$ and 10 mM phosphate buffer solution of homo-P(Asp-AP-cyst)$_{48}$ were independently prepared (in this working example, every polymer concentration is 1 mg/mL). The solutions were mixed together so that the ratio of the number of positive and negative charges contained in the solution became equal, that is, the number of —COO$^{31}$ became equal to the number of —NH$_3^+$, and the mixture was stirred for 2 minutes to obtain PICsome (see FIG. 4). FIG. 4 is a schematic view of PICsome preparation scheme. By mixing homo-polycation and PEG-polyanion, PICsome can be obtained. Note that in FIG. 4(a), "m" and "n" in copolymer represent the polymerization number (m=45, n=75 or 85). In FIG. 4(b), "m" and "n" in copolymer represent the polymerization number (m=38, n=10).

The PICsome was identified by observation using a transmission electron microscope (TEM) and the measurement of dynamic light scattering (DLS) as described below. In order to crosslink the polyion complex (PIC) membrane of the obtained PICsome, an EDC solution (10 mg/mL) was added in an amount of 10 equivalents of the —COO$^-$ side chain. As a comparative example, a PICsome containing no disulfide was prepared using homo-P(Asp-AP) instead of homo-P (Asp-AP-Cyst).

<Continuation of PICsome Structure by TEM Observation>

The structure of the PICsome produced by the above-described process was confirmed using a transmission electron microscope (TEM). After crosslinking, the produced PICsome was subjected to uranyl staining, dried on a TEM grid, and then it was observed. For observation, a transmission electron microscope H-7000 manufactured by Hitachi was used.

Figure 5:
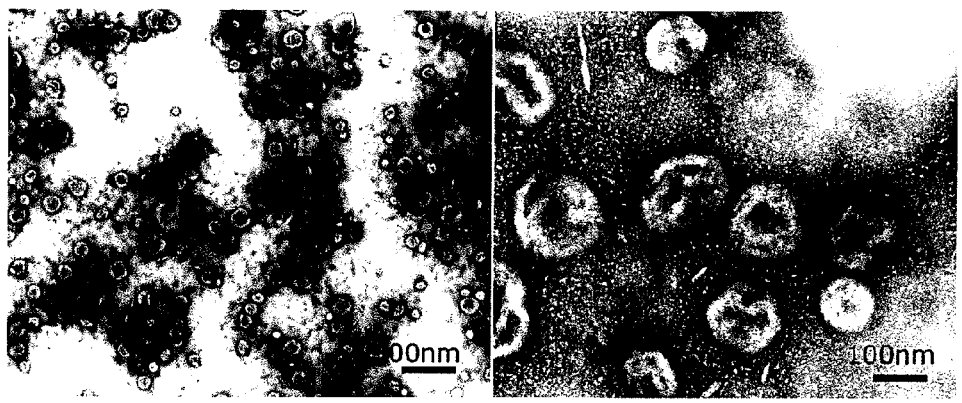
FIG. 5 shows photographs of transmission electron microscope observation of the vesicle of the present invention.
Figure 5:
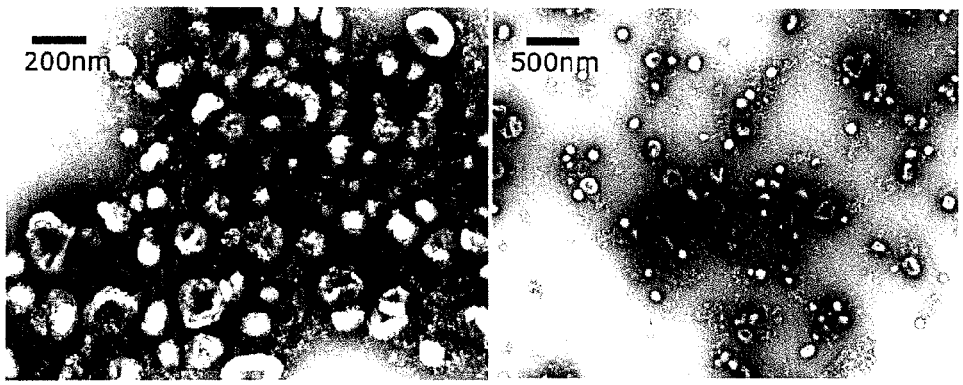

As a result, it was suggested that the disulfide-containing PICsome is a unilamellar vesicle (FIG. 5).

FIG. 5 shows photographs of TEM observation of the obtained PICsome (photographed after stained with uranyl acetate).

Images specific to the vesicle-derived hollow structure (vision corresponding to the fact that the hollow site dents due to drying) were confirmed.

(a): Cyst 20%-PICsome: (+) homo-P(Asp-AP$_{0.8}$-Cyst$_{0.2}$)$_{48}$/ (−) PEG-P(Asp)$_{85}$
(b): Cyst 45%-PICsome: (+) homo-P(Asp-AP$_{0.55}$-Cyst$_{0.45}$)$_{45}$/(−) PEG-P(Asp)$_{85}$ <Confirmation of Salt Stability of PICsome by DLS Measurement>

In order to assess the stability of the disulfide-containing PICsome under physiological conditions, regarding the previously prepared Cyst 45%-PICsome (10 mM phosphate buffer; 0 mM NaCl, pH 7.4, 25° C.), influence of addition of 150 mM NaCl on particles was assessed by measuring the particle size (diameter) using a dynamic light scattering (DLS) analyzer.

Figure 6:
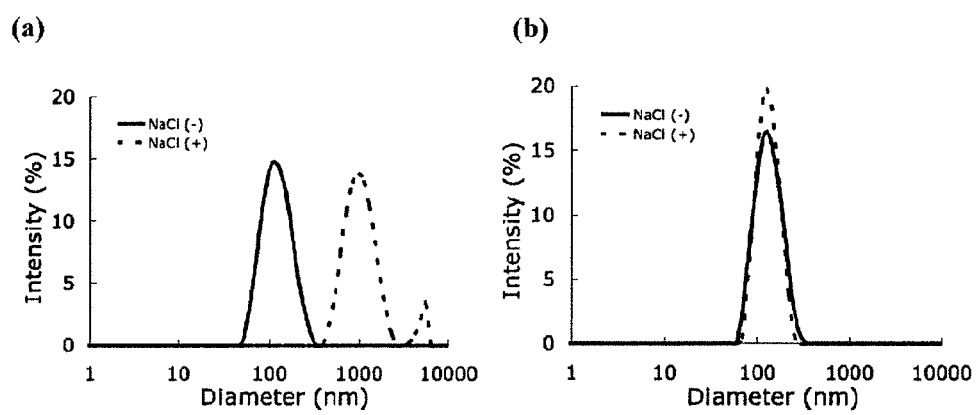
FIG. 6 shows the measurement results of the particle diameter of the vesicle of the present invention.

As a result, it was confirmed that the salt stability is imparted by performing appropriate EDC crosslinking (addition of EDC in an amount of 1 equivalent or more of the side chain —COO$^−$) (FIG. 6).

FIG. 6 shows the DLS measurement results corresponding to the presence or absence of the addition of 150 mM NaCl. Regarding Cyst 45%-PICsome, the cases of (a) without crosslinking and (b) after crosslinking (addition of 10 equivalents of EDC) were measured. After crosslinking, even when NaCl was added, the particle diameter was not changed.

<Assessment of Responsiveness of Disulfide-Containing PICsome (Noncrosslinked Type) to Reducing Agent by DLS>

The responsiveness of the noncrosslinked Cyst 45%-PICsome to a reducing agent was assessed by conducting the DLS measurement after addition of DTT solution. Reduction by DTT was conducted by adding 20 mM DTT solution in an amount which is 25% of the total amount of the PICsome solution.

Figure 7:
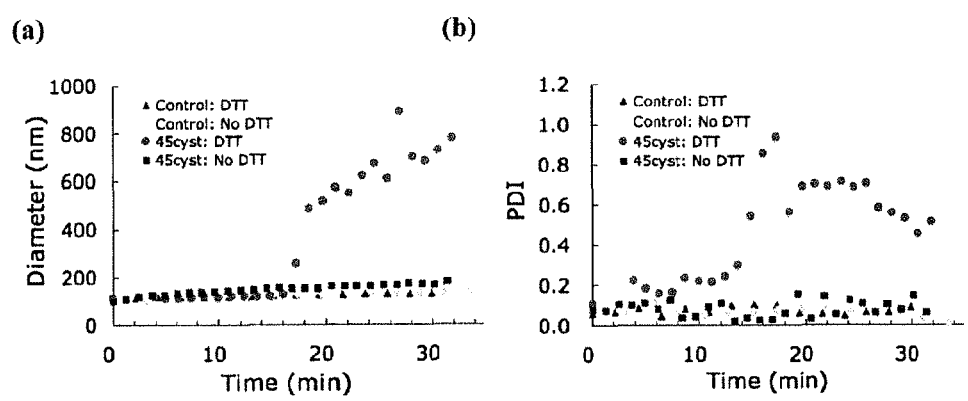
FIG. 7 shows the measurement results of time-dependent change in the particle diameter of the vesicle of the present invention.

FIG. 7 shows results of comparison examination using Cyst 45%-PICsome containing disulfides and Cyst 0%-PICsome containing no disulfide [(+) homo-P(Asp-AP)$_{82}$/(−) PEG-P(Asp)$_{85}$].

FIG. 7 shows results of the measurement of DLS in 10 mM phosphate buffer (0 mM NaCl, pH 7.4, 25° C.), and shows time-dependent change in (a) particle diameter and (b) polydispersity index (PDI) before and after addition of 20 mM DTT.

Control: Cyst 0%-PICsome
45cyst: Cyst 45%-PICsome

In the case of Cyst 0%-PICsome, time-dependent change in the particle diameter and PDI was not observed before and after addition of DTT, whereas in the case of Cyst 45%-PICsome, the particle diameter and PDI were rapidly increased sometime after addition of DTT. Thus, the responsiveness of the disulfide-containing PICsome to the reduction environment was confirmed.

<Assessment of Responsiveness of Disulfide-Containing PICsome (Crosslinked Type) to Reducing Agent by DLS>

Figure 8:
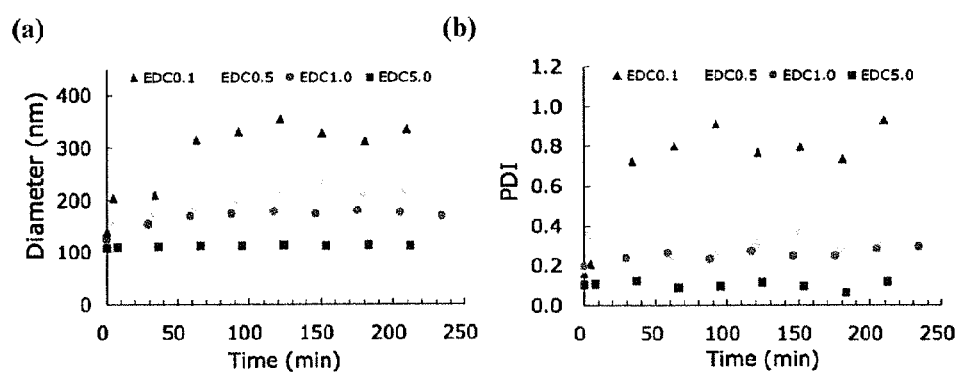
FIG. 8 shows the measurement results of time-dependent change in the particle diameter and PDI of the vesicle of the present invention.

The responsiveness of the crosslinked Cyst 45%-PICsome to a reducing agent was assessed by conducting the DLS measurement after addition of DTT solution. The adding amount of EDC was changed from 0.1 to 5.0 equivalents to prepare 4 types of crosslinking (FIG. 8). The addition of DTT was conducted by adding 20 mM DTT solution in an amount which is 25% of the total amount of the PICsome solution.

FIG. 8 shows results of the measurement of DLS in 10 mM phosphate buffer (0 mM NaCl, pH 7.4, 25° C.), and shows time-dependent change in (a) particle diameter and (b) PDI after addition of 20 mM DTT (EDC 0.1: 0.1 equivalent of EDC, EDC 0.5: 0.5 equivalent of EDC, EDC 1.0: 1.0 equivalent of EDC, and EDC 5.0: 5.0 equivalents of EDC). Both the particle diameter and PDI were affected in some way by DTT addition except in the case of addition of 5.0 equivalents of EDC. Only in the case of addition of 5.0 equivalents of EDC, the particle diameter and PDI were not affected by DTT addition and were constant. Thus, it was suggested that the vesicle of the present invention is a material whose responsiveness varies depending on the crosslinking state.

<Assessment of Responsiveness of Crosslinked PICsome to Reducing Agent by FCS>

The responsiveness of the crosslinked Cyst 58%-PICsome to a reducing agent was assessed by conducting the fluorescence correlation spectroscopy (FCS) measurement after addition of DTT solution. A fluorescently-labeled PICsome was produced using PEG-P(Asp)$_{75}$-Cy3 in which the terminus of PEG-P(Asp)$_{75}$ had been fluorescently labeled with Cy3. To each of the fluorescently-labeled Cyst 58%-PICsome and the fluorescently-labeled Cyst 0%-PICsome, 5 equivalents of EDC was added to provide crosslinking. Reduction by DTT was conducted by adding 5 mM DTT solution in an amount which is 25% of the total amount of the PICsome solution. The FCS measurement was conducted three times at an excitation wavelength of 543 nm.

Figure 9:
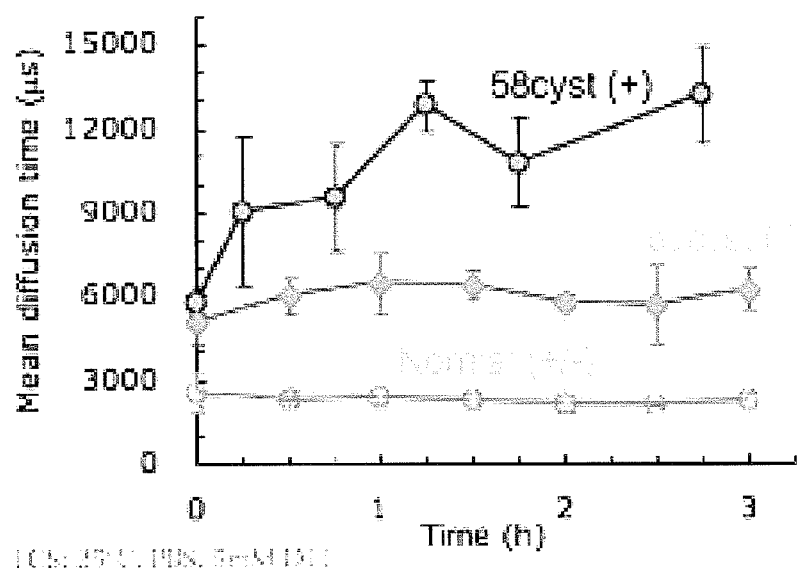
FIG. 9 shows the FCS measurement results of the vesicle of the present invention.

FIG. 9 shows the measurement results of FCS in 10 mM phosphate buffer (150 mM NaCl, pH 7.4, 25° C.), and shows time-dependent change in the translational diffusion time under conditions with or without addition of 5 mM DTT.

58cyst (+): Cyst 58%-PICsome+DTT
58cyst (−): Cyst 58%-PICsome
Normal (+/−): Cyst 0%-PICsome (+/−) DTT In the case of Cyst 0%-PICsome, time-dependent change in the translational diffusion time was not observed with or without addition of DTT, whereas in the case of Cyst 58%-PICsome, the translational diffusion time was gradually increased only when DTT was added.

Thus, it was suggested that the vesicle of the present invention shows responsiveness to the reduction environment.

EXAMPLE 2

Production of Vesicle 2
<Materials>

(R)-2-amino-3-(4-methoxybenzylthio)propanoic acid (H-Cys(Mob)-OH) was purchased from Sigma (St. Louis, Colo., USA). Triphosgene, Tributylphosphine, 3-Nitro-2-pyridinesulfenyl chloride (NpysCl), 2-iminothiolane, Diisopropylethylamine, dehydrated THF, dehydrated DMF, dehydrated NMP and dehydrated CH$_2$Cl$_2$ were purchased from Wako Pure Chemical Industries, Ltd. (Osaka). α-methoxy-ω-amino poly(ethylene glycol)(PEG-NH$_2$) (molecular weight: 2,000) was purchased from NOF Corporation (Tokyo). n-Butylamine (Bu-NH$_2$) was distilled and then it was used. 1,5-diaminopentane (DAP) was purchased from Tokyo Chemical Industry Co., Ltd. (Tokyo).

<Synthesis of Carboxylic Acid Anhydride of Protected Cysteine>

4 g of H-Cys(Mob)-OH was dissolved in THF, and it was reacted with 2 equivalents of triphosgene at 50° C. for 2 hours, and the obtained solution was precipitated using hexane. The obtained precipitate was dissolved in CH$_2$Cl$_2$, and it was purified by recrystallization using hexane. It was confirmed from LC-MS and $^1$H NMR that 4-methoxybenzylcysteine N-carboxy anhydride (Cys(Mob)-NCA) was synthesized.

<Synthesis of Protected Thiol-Containing Block Copolymer>

To 100 mg of PEG-NH$_2$ which had been lyophilized to remove water, 5 mL of mixed solvent of DMF/CH$_2$Cl$_2$ (=1:4) was added to obtain a PEG-NH$_2$ solution. Further, using a syringe, a solution obtained by adding 10 equivalents of Cys(Mob)-NCA to 5 mL of mixed solvent of DMF/CH$_2$Cl$_2$ (=1:

4) was added to the PEG-NH$_2$ solution in an eggplant flask with stirring. The solution in the eggplant flask was reacted for a day with stirring at 35° C.

To another eggplant flask, 790 mg (90 equivalents) of BLA-NCA synthesized using β-benzyl-L-aspartate as a raw material and 25 mL of mixed solvent of DMF/CH$_2$Cl$_2$ (=1:4) were added to obtain a solution in a manner similar to that of the above-described Cys(Mob)-NCA. Using a syringe, the solution was added to the above-described reaction solution with stirring. The mixture was reacted for 2 days with stirring at 35° C. After a predetermined amount of time, to the reaction solution, about 5 times its volume of ether was added to obtain a precipitate. The precipitate was filtered and washed with ether several times. After that, the obtained product was dried under reduced pressure, thereby obtaining a block copolymer PEG-PCys(Mob)-PBLA.

PEG-PCys(Mob)-PBLA was subjected to the $^1$H NMR measurement, and based on the proton ratio between the peaks at about 7 and 7.8 ppm derived from the Mob group and the PEG ethylene chain peak, it was estimated that the polymerization number of PCys(Mob) is about 9, and that the polymerization number of PBLA is about 80. Further, using size exclusion chromatography, a monomodal peak was confirmed, and appropriate reaction progress was confirmed. By changing the blend ratio of raw materials, it is possible to synthesize a block copolymer in which the polymerization number of PCys(Mob) is 5 to 30 and the polymerization number of PBLA is 30 to 150.

<Synthesis of Thiol-Containing Block Copolymer>

To 100 mg of the synthesized PEG-PCys(Mob)-PBLA, 10 mL of CH$_2$Cl$_2$ and 30 mg (3 equivalents) of NpysCl were added, and the mixture was reacted at room temperature for 5 hours, and a 4-methoxybenzyl (Mob) group that is a protective group of cysteine was substituted with a 3-Nitro-2-pyridinesulfenyl (Npys) group. Subsequently, to the reaction solution, 200 µl of tributylphosphine was added, and the mixture was reacted at room temperature for 10 minutes. To the obtained reaction solution, about 5 times its volume of ether was added to obtain a precipitate. The precipitate was filtered and washed with ether several times. After that, the obtained product was dried under reduced pressure, thereby obtaining a thiol-containing block copolymer PEG-PCys-PBLA.

The obtained product was subjected to the $^1$H NMR measurement. The peaks at about 7-9 ppm derived from the Mob group and the Npys group were lost, and deprotection reaction of the thiol group was confirmed.

<Synthesis of Thiol-Containing Anionic Block Copolymer>

100 mg of the synthesized PEG-PCys-PBLA was dissolved in a small amount of acetonitrile, and subsequently, 10 ml of 1 M NaOH solution was added thereto, and the mixture was stirred at room temperature for 1 hour. The obtained reaction solution was put into a dialysis tube (MWCO 3,500), and dialysis was performed for 3 days using distilled water as an external solution. The external solution was exchanged several times, and an internal solution was collected and then lyophilized, thereby obtaining a thiol-containing anionic block copolymer PEG-PCys-PAsp.

PEG-PCys-PAsp was subjected to the $^1$H NMR measurement. Based on the proton ratio between the PEG ethylene chain peak at about 3.5 ppm and the methylene peaks of PAsp and PCys at about 2.6 ppm, it was calculated that the total polymerization number of PAsp and PCys is about 85. It was confirmed from this result that deprotection reaction of PBLA progressed quantitatively.

<Synthesis of Thiol-Containing Polymer>

To 365 µL of DMF solution of Bu-NH$_2$ (10 mg/mL), 10 mL of mixed solvent of DMF/CH$_2$Cl$_2$ (=1:4) was added. Further, using a syringe, a solution obtained by adding 10 mL of separately prepared mixed solvent of DMF/CH$_2$Cl$_2$ (=1:4) and 134 mg (10 equivalents) of Cys(Mob)-NCA was added to a Bu-NH$_2$ solution in an eggplant flask with stirring. The solution in the eggplant flask was reacted for a day with stirring at 35° C.

To another eggplant flask, 1122 mg (90 equivalents) of BLA-NCA and 20 mL of mixed solvent of DMF/CH$_2$Cl$_2$ (=1:4) were added, and using a syringe, the thus obtained solution was added to the above-described reaction solution with stirring. The mixture was reacted for 2 days with stirring at 35° C. After a predetermined amount of time, to the reaction solution, about 5 times its volume of ether was added to obtain a precipitate. The precipitate was filtered and washed with ether several times. After that, the obtained product was lyophilized, thereby obtaining a protected thiol-containing polymer PCys(Mob)-PBLA.

PCys(Mob)-PBLA was subjected to the $^1$H NMR measurement. Based on the proton ratio between the peaks at about 7 and 7.8 ppm derived from the Mob group and the peak derived from the terminal butyl group, it was estimated that the polymerization number of PCys(Mob) is about 10, and that the polymerization number of PBLA is about 95. Further, using size exclusion chromatography, a monomodal peak was confirmed, and appropriate reaction progress was confirmed. By changing the blend ratio of raw materials, it is possible to synthesize an amino acid polymer in which the polymerization number of PCys(Mob) is 5 to 30 and the polymerization number of PBLA is 30 to 150.

To 200 mg of the obtained PCys(Mob)-PBLA, 10 mL of CH$_2$Cl$_2$ and 30 mg (3 equivalents) of NpysCl were added, and the mixture was reacted at room temperature for 5 hours, and the Mob group that is a protective group of cysteine was substituted with the Npys group. Subsequently, to the reaction solution, 200 µl of tributylphosphine was added, and the mixture was reacted at room temperature for 10 minutes. To the obtained reaction solution, about 5 times its volume of ether was added to obtain a precipitate. The precipitate was filtered and washed with ether several times. After that, the obtained product was dried under reduced pressure, thereby obtaining a thiol-containing polymer PCys-PBLA.

The obtained product was subjected to the $^1$H NMR measurement. The peaks at about 7-9 ppm derived from the Mob group and the Npys group were lost, and deprotection reaction of the thiol group was confirmed.

<Synthesis of Thiol-Containing Cationic Amino Acid Polymer>

The collected thiol-containing polymer PCys-PBLA was dissolved in 2.5 mL of NMP, and subsequently DAP (25 to 40 equivalents of PBLA) was added to the solution, and the mixture was vigorously stirred at 5° C. for 1 hour. The reaction mixture was neutralized with 20 wt % acetic acid at 0 to 5° C., and it was dialyzed against 0.01 M hydrochloric acid for 3 days and subsequently against pure water for 3 days. The internal solution was collected by lyophilization, thereby obtaining a thiol-containing cationic amino acid polymer PCys-P(Asp-AP).

PCys-P(Asp-AP) was subjected to the $^1$H NMR measurement. Based on the proton ratio between the PEG ethylene chain peak at about 3.5 ppm and the methylene peaks of PAsp and PCys at about 2.6 ppm, it was calculated that the total polymerization number of PAsp and PCys is about 100. It was confirmed from this result that deprotection reaction of PBLA progressed quantitatively.

<Preparation and Oxidation of Thiol-Containing Vesicle (PICsome)>

The anionic copolymer and the cationic amino acid polymer synthesized as described above were subjected to TCEP (Tris(2-carboxyethyl)phosphine) reduction, and purified using a PD-10 Desalting Column and then lyophilized. Using the obtained products, a thiol-containing vesicle was prepared.

10 mM phosphate buffer (0 mM NaCl, pH 7.4) solution of the anionic copolymer PEG-PCys-PAsp and 10 mM phosphate buffer solution of the cationic amino acid polymer PCys-P(Asp-AP) were independently prepared (in this working example, every polymer concentration is 1 mg/mL). The solutions were mixed together so that the ratio of the number of positive and negative charges contained in the solution became equal, that is, the number of $-COO^-$ became equal to the number of $-NH_3^+$, and the mixture was stirred for 2 minutes to obtain PICsome.

Figure 10:
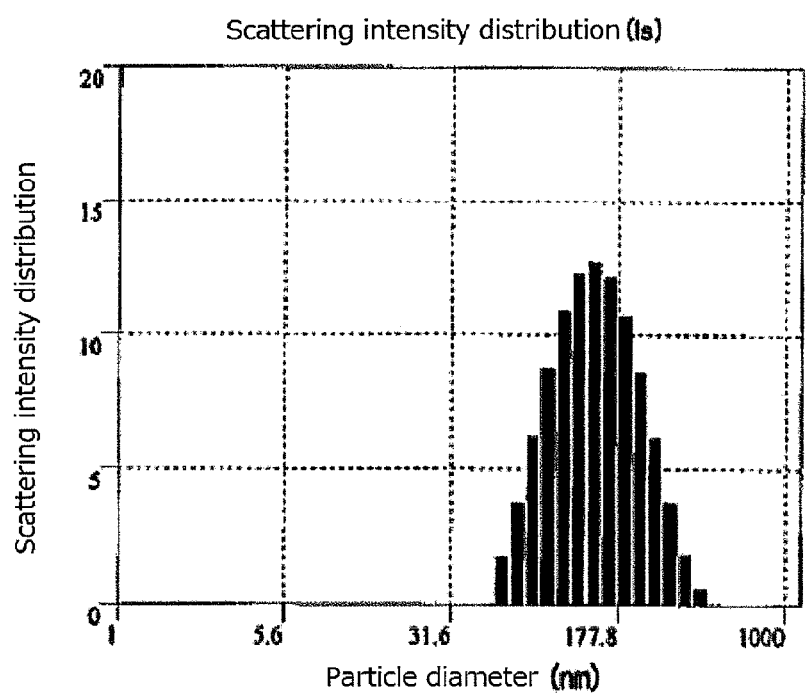
FIG. 10 shows the DLS measurement results of the thiol-containing vesicle of the present invention.

The particle diameter of the PICsome was measured by DLS. The result is shown in FIG. 10. In the obtained suspension of the PICsome, air oxidation progressed spontaneously, and it was confirmed that the disulfide bond was formed and stable under physiological conditions.

Hereinafter, in Examples 3-5, examples of synthesis of the first polymer and the second polymer are described.

EXAMPLE 3

<Synthesis of Thiol-Containing Anionic Block Copolymer>

To 100 mg of PEG-NH$_2$ which had been lyophilized to remove water, 5 mL of mixed solvent of DMF/CH$_2$Cl$_2$ (=1:4) was added to obtain a PEG-NH$_2$ solution. Further, using a syringe, a solution obtained by adding 133.65 mg (10 equivalents) of Cys(Mob)-NCA and 1121.49 mg (90 equivalents) of BLA-NCA to 25 mL of mixed solvent of DMF/CH$_2$Cl$_2$ (=1:4) was added to the PEG-NH$_2$ solution in an eggplant flask with stirring. The solution in the eggplant flask was reacted for 2 days with stirring at 35° C. After a predetermined amount of time, to the reaction solution, about 5 times its volume of ether was added to obtain a precipitate. The precipitate was filtered and washed with ether several times. After that, the obtained product was dried under reduced pressure, thereby obtaining a block copolymer PEG-P(BLA-r-Cys(Mob)).

Note that "-r-" in the formula means that cysteine is randomly placed in the main chain of the amino acid.

PEG-P(BLA-r-Cys(Mob)) was subjected to the $^1$H NMR measurement, and based on the proton ratio between the peaks at about 7 and 7.8 ppm derived from the Mob group and the PEG ethylene chain peak, it was estimated that the polymerization number of PCys(Mob) is about 9, and that the polymerization number of PBLA is about 88. By changing the blend ratio of raw materials, it is possible to synthesize a block copolymer in which the polymerization number of PCys(Mob) is 5 to 30 and the polymerization number of PBLA is 30 to 150. Further, using size exclusion chromatography, a monomodal peak was confirmed, and appropriate reaction progress was confirmed.

To 200 mg of the synthesized PEG-P(BLA-r-Cys(Mob)), 10 mL of CH$_2$Cl$_2$ and 30 mg (3 equivalents) of NpysCl were added, and the mixture was reacted at room temperature for 5 hours, and the Mob group that is a protective group of cysteine was substituted with the Npys group. Subsequently, to the reaction solution, 200 µl of tributylphosphine was added, and the mixture was reacted at room temperature for 10 minutes. To the obtained reaction solution, about 5 times its volume of ether was added to obtain a precipitate. The precipitate was filtered and washed with ether several times. After that, the obtained product was dried under reduced pressure, thereby obtaining a thiol-containing block copolymer PEG-P(BLA-r-Cys).

The obtained product was subjected to the $^1$H NMR measurement. The peaks at about 7-9 ppm derived from the Mob group and the Npys group were lost, and deprotection reaction of the thiol group was confirmed.

100 mg of the synthesized PEG-P(BLA-r-Cys) was dissolved in a small amount of acetonitrile, and subsequently, 10 mL of 1 M NaOH solution was added thereto, and the mixture was stirred at room temperature for 1 hour. The obtained reaction solution was put into a dialysis tube (MWCO 3,500), and dialysis was performed for 3 days using distilled water as an external solution. The external solution was exchanged several times, and an internal solution was collected and then lyophilized, thereby obtaining a thiol-containing anionic block copolymer PEG-P(Asp-r-Cys).

PEG-P(Asp-r-Cys) was subjected to the $^1$H NMR measurement. Based on the proton ratio between the PEG ethylene chain peak at about 3.5 ppm and the methylene peaks of PAsp and PCys at about 2.6 ppm, it was calculated that the total polymerization number of PAsp and PCys is about 90. It was confirmed from this result that deprotection reaction of PBLA progressed quantitatively.

<Synthesis of Thiol-Containing Cationic Amino Acid Polymer>

To 366 µL of DMF solution of Bu-NH$_2$ (10 mg/mL), 10 mL of mixed solvent of DMF/CH$_2$Cl$_2$ (=1:4) was added. Further, using a syringe, a solution obtained by adding 134 mg (10 equivalents) of Cys(Mob)-NCA and 1121 mg (90 equivalents) of BLA-NCA to 25 mL of separately prepared mixed solvent of DMF/CH$_2$Cl$_2$ (=1:4) was added to a Bu-NH$_2$ solution in an eggplant flask with stirring. The solution in the eggplant flask was reacted for 2 days with stirring at 35° C. After a predetermined amount of time, to the reaction solution, about 5 times its volume of ether was added to obtain a precipitate. The precipitate was filtered and washed with ether several times. After that, the obtained product was dried under reduced pressure, thereby obtaining a protected thiol-containing polymer P(BLA-r-Cys(Mob)).

P(BLA-r-Cys(Mob)) was subjected to the $^1$H NMR measurement, and based on the proton ratio between the peaks at about 7 and 7.8 ppm derived from the Mob group and the peak derived from the terminal butyl group, it was estimated that the polymerization number of PCys(Mob) is about 10, and that the polymerization number of PBLA is about 95. By changing the blend ratio of raw materials, it is possible to synthesize a polymer in which the polymerization number of PCys(Mob) is 5 to 30 and the polymerization number of PBLA is 30 to 150. Further, using size exclusion chromatography, a monomodal peak was confirmed, and appropriate reaction progress was confirmed.

To 200 mg of the obtained P(BLA-r-Cys(Mob)), 10 mL of CH$_2$Cl$_2$ and 30 mg (3 equivalents) of NpysCl were added, and the mixture was reacted at room temperature for 5 hours, and the Mob group that is a protective group of cysteine was substituted with the Npys group. Subsequently, to the reaction solution, 200 mL of tributylphosphine was added, and the mixture was reacted at room temperature for 10 minutes. To the obtained reaction solution, about 5 times its volume of ether was added to obtain a precipitate. The precipitate was filtered and washed with ether several times. After that, the obtained product was dried under reduced pressure, thereby obtaining a thiol-containing polymer P(BLA-r-Cys).

The obtained product was subjected to the $^1$H NMR measurement. The peaks at about 7-9 ppm derived from the Mob group and the Npys group were lost, and deprotection reaction of the thiol group was confirmed.

The collected product was dissolved in 2.5 mL of NMP, and DAP (25 to 40 equivalents of PBLA) was added to the solution, and the mixture was vigorously stirred at 5° C. for 1 hour. The reaction mixture was neutralized with 20 wt % acetic acid at 0 to 5° C., and it was dialyzed against 0.01 M hydrochloric acid for 3 days and subsequently against pure water for 3 days. The internal solution was collected by lyophilization, thereby obtaining a thiol-containing cationic amino acid polymer P((Asp-AP)-r-Cys). P((Asp-AP)-r-Cys) was subjected to the $^1$H NMR measurement. Based on the proton ratio between the peak derived from the terminal butyl group and the methylene peaks of P(Asp-AP) and PCys at about 2.6 ppm, it was calculated that the total polymerization number of P(Asp-AP) and PCys is about 100. It was confirmed from this result that deprotection reaction of PBLA progressed quantitatively.

EXAMPLE 4

<Synthesis of Thiol-Containing Anionic Block Copolymer>

To 100 mg of PEG-NH$_2$ which had been lyophilized to remove water, 5 mL of mixed solvent of DMF/CH$_2$Cl$_2$ (=1:4) was added to obtain a PEG-NH$_2$ solution. Further, using a syringe, a solution obtained by adding 133.65 mg (10 equivalents) of Cys(Mob)-NCA to 5 mL of mixed solvent of DMF/CH$_2$Cl$_2$ (=1:4) was added to the PEG-NH$_2$ solution in an eggplant flask with stirring. The solution in the eggplant flask was reacted for a day with stirring at 35° C.

To another eggplant flask, 996.88 mg (80 equivalents) of BLA-NCA and 25 mL of mixed solvent of DMF/CH$_2$Cl$_2$ (=1:4) were added to obtain a solution. Using a syringe, the solution was added to the above-described reaction solution with stirring. The mixture was reacted for 2 days with stirring at 35° C.

After that, to another eggplant flask, 133.65 mg (10 equivalents) of Cys(Mob)-NCA and 5 mL of mixed solvent of DMF/CH$_2$Cl$_2$ (=1:4) were added to obtain a solution. Using a syringe, the solution was added to the above-described reaction solution with stirring. The mixture was reacted for a day with stirring at 35° C.

After a predetermined amount of time, to the reaction solution, about 5 times its volume of ether was added to obtain a precipitate. The precipitate was filtered and washed with ether several times. After that, the obtained product was dried under reduced pressure, thereby obtaining a block copolymer PEG-PCys(Mob)-PBLA-PCys(Mob).

PEG-PCys(Mob)-PBLA-PCys(Mob) was subjected to the $^1$H NMR measurement, and based on the proton ratio between the peaks at about 7 and 7.8 ppm derived from the Mob group and the PEG ethylene chain peak, it was estimated that the polymerization number of PCys(Mob) is about 18, and that the polymerization number of PBLA is about 75. By changing the blend ratio of raw materials, it is possible to synthesize a block copolymer in which the polymerization number of PCys(Mob) is 5 to 30 and the polymerization number of PBLA is 30 to 150. Further, using size exclusion chromatography, a monomodal peak was confirmed, and appropriate reaction progress was confirmed.

To 200 mg of the synthesized PEG-PCys(Mob)-PBLA-PCys(Mob), 10 mL of CH$_2$Cl$_2$ and 60 mg (3 equivalents) of NpysCl were added, and the mixture was reacted at room temperature for 5 hours, and the Mob group that is a protective group of cysteine was substituted with the Npys group. Subsequently, to the reaction solution, 400 µL of tributylphosphine was added, and the mixture was reacted at room temperature for 10 minutes. To the obtained reaction solution, about 5 times its volume of ether was added to obtain a precipitate. The precipitate was filtered and washed with ether several times. After that, the obtained product was dried under reduced pressure, thereby obtaining a thiol-containing block copolymer PEG-PCys-PBLA-PCys.

The obtained product was subjected to the $^1$H NMR measurement. The peaks at about 7-9 ppm derived from the Mob group and the Npys group were lost, and deprotection reaction of the thiol group was confirmed.

100 mg of the synthesized PEG-PCys-PBLA-PCys was dissolved in a small amount of acetonitrile, and subsequently, 10 mL of 1 M NaOH solution was added thereto, and the mixture was stirred at room temperature for 1 hour. The obtained reaction solution was put into a dialysis tube (MWCO 3,500), and dialysis was performed for 3 days using distilled water as an external solution. The external solution was exchanged several times, and an internal solution was collected and then lyophilized, thereby obtaining a thiol-containing anionic block copolymer PEG-PCys-PAsp-PCys.

PEG-PCys-PAsp-PCys was subjected to the $^1$H NMR measurement. Based on the proton ratio between the PEG ethylene chain peak at about 3.5 ppm and the methylene peaks of PAsp and PCys at about 2.6 ppm, it was calculated that the total polymerization number of PAsp and PCys is about 90. It was confirmed from this result that deprotection reaction of PBLA progressed quantitatively.

<Synthesis of Thiol-Containing Cationic Amino Acid Polymer>

To 365 µL of DMF solution of Bu-NH$_2$ (10 mg/mL), 10 mL of mixed solvent of DMF/CH$_2$Cl$_2$ 1:4) was added. Further, using a syringe, a solution obtained by adding 134 mg (10 equivalents) of Cys(Mob)-NCA to 10 mL of separately prepared mixed solvent of DMF/CH$_2$Cl$_2$ (−1:4) was added to a Bu-NH$_2$ solution in an eggplant flask with stirring. The solution in the eggplant flask was reacted for a day with stirring at 35° C.

To another eggplant flask, 996.88 mg (80 equivalents) of BLA-NCA and 20 mL of mixed solvent of DMF/CH$_2$Cl$_2$ (=1:4) were added to obtain a solution. Using a syringe, the solution was added to the above-described reaction solution with stirring. The mixture was reacted for 2 days with stirring at 35° C.

After that, to another eggplant flask, 133.65 mg (10 equivalents) of Cys(Mob)-NCA and 5 mL of mixed solvent of DMF/CH$_2$Cl$_2$ (=1:4) were added to obtain a solution. Using a syringe, the solution was added to the above-described reaction solution with stirring. The mixture was reacted for a day with stirring at 35° C.

After a predetermined amount of time, to the reaction solution, about 5 times its volume of ether was added to obtain a precipitate. The precipitate was filtered and washed with ether several times. After that, the obtained product was dried under reduced pressure, thereby obtaining a polymer PCys (Mob)-PBLA-PCys(Mob).

PCys(Mob)-PBLA-PCys(Mob) was subjected to the $^1$H NMR measurement, and based on the proton ratio between the peaks at about 7 and 7.8 ppm derived from the Mob group and the peak derived from the terminal butyl group, it was estimated that the polymerization number of PCys(Mob) is about 16, and that the polymerization number of PBLA is about 80. By changing the blend ratio of raw materials, it is possible to synthesize a polymer in which the polymerization number of PCys(Mob) is 5 to 30 and the polymerization number of PBLA is 30 to 150. Further, using size exclusion chromatography, a monomodal peak was confirmed, and appropriate reaction progress was confirmed.

To 200 mg of the obtained PCys(Mob)-PBLA-PCys (Mob), 10 mL of $CH_2Cl_2$ and 60 mg (3 equivalents) of Npy-sCl were added, and the mixture was reacted at room temperature for 5 hours, and the Mob group that is a protective group of cysteine was substituted with the Npys group. Subsequently, to the reaction solution, 400 μL of tributylphosphine was added, and the mixture was reacted at room temperature for 10 minutes. To the obtained reaction solution, about 5 times its volume of ether was added to obtain a precipitate. The precipitate was filtered and washed with ether several times. After that, the obtained product was dried under reduced pressure, thereby obtaining a thiol-containing polymer PCys-PBLA-PCys.

The obtained product was subjected to the $^1$H NMR measurement. The peaks at about 7-9 ppm derived from the Mob group and the Npys group were lost, and deprotection reaction of the thiol group was confirmed.

The collected thiol-containing polymer PCys-PBLA-PCys was dissolved in 2.5 mL of NMP, and DAP (25 to 40 equivalents of PBLA) was added to the solution, and the mixture was vigorously stirred at 5° C. for 1 hour. The reaction mixture was neutralized with 20 wt % acetic acid at 0 to 5° C., and it was dialyzed against 0.01 M hydrochloric acid for 3 days and subsequently against pure water for 3 days. The internal solution was collected by lyophilization, thereby obtaining a thiol-containing cationic amino acid polymer PCys-P(Asp-AP)-PCys.

PCys-P(Asp-AP)-PCys was subjected to the $^1$H NMR measurement. Based on the proton ratio between the peak derived from the terminal butyl group and the methylene peaks of P(Asp-AP) and PCys at about 2.6 ppm, it was calculated that the total polymerization number of P(Asp-AP) and PCys is about 90. It was confirmed from this result that deprotection reaction of PBLA progressed quantitatively.

EXAMPLE 5

<Synthesis of Cationic Amino Acid Polymer Containing Thiol at the Side-Chain Terminus>

A synthesized homo-P(Asp-AP) (DP=77, 75 mg) was dissolved in 2 mL of NMP, and subsequently 58.2 mg of 2-iminothiolane and 250 μL of diisopropylethylamine were added to the solution, and the mixture was stirred at room temperature for about 1 hour. Subsequently, to the reaction solution, 100 mg of LiCl was added and the mixture was stirred for about 1 hour. The reaction mixture was neutralized with 0.01 M hydrochloric acid, and it was dialyzed against pure water for 3 days.

The obtained solution was lyophilized, thereby obtaining a cationic amino acid polymer P(Asp-AP-IM), which contains a 1-imino-4-mercaptobutyl (IM) group at the side-chain amino terminus. Using size exclusion chromatography, a monomodal peak was confirmed, and appropriate reaction progress was confirmed. Further, based on $^1$H NMR, it was confirmed that nearly 100% of the raw material homo-P(Asp-AP) was reacted. By changing the amount of 2-iminothiolane to be added, it is possible to control the IM introduction ratio in the range from 0 to 100%.

EXAMPLE 6

Production of Vesicle 3

<Materials>

1,2-dithiane-4,5-diol was purchased from Tokyo Chemical Industry Co., Ltd. (Tokyo).
<Synthesis of Cyclic Disulfide>

1,2-dithiane-t-4,t-5-diol r-1-oxide was synthesized using 1,2-dithiane-4,5-diol as a raw material according to the method described in a document (Pramod K. S. et al., J. Org. Chem., 1988, 53, 2608-2612).
<Production of Disulfide-Crosslinked Type Vesicle (PICsome)>

10 mM phosphate buffer (0 mM NaCl, pH 7.4) solution of PEG-PCys-PAsp and 10 mM phosphate buffer solution of PCys-P(Asp-AP) (1 mg/mL) were independently prepared. The solutions were mixed together so that the ratio of the number of positive and negative charges contained in the solution became equal, that is, the number of $-COO^-$ became equal to the number of $-NH_3^+$, and the mixture was stirred for 2 minutes to obtain PICsome.

To this PICsome solution, 1,2-dithiane-t-4,t-5-diol r-1-oxide was added in an amount of 0.5 to 10 equivalents of the thiol group at the PEG-PCys-PAsp side, thereby crosslinking the polymers.

EXAMPLE 7

Production and Assessment of Cytochrome c-Encapsulated Vesicle
<Materials>

2,2'-azino-bis(3-ethylbenzothiazoline-6-sulfonic acid) (ABTS) was purchased from Sigma (St. Louis, Colo., USA). Hydrogen peroxide ($H_2O_2$) was purchased from Wako Pure Chemical Industries, Ltd. (Osaka). PD-10 Desalting Column was purchased from GE Healthcare.
<Encapsulation of Substance in Disulfide-Containing Vesicle (PICsome) According to the Vortex Process>

The suspension of the disulfide-containing vesicle, 45cyst PICsome produced in Example 1 was again stirred by vortex, and with that, a phosphate buffer solution of cytochrome c (12.4 mg/mL) was added thereto (5 v/v (%)) to allow cytochrome c to be encapsulated in the PICsome. An EDC solution (10 equivalents of $-COO^-$ side chain) was added thereto, and the mixture was reacted at 4° C. overnight. Excess amounts of EDC and unencapsulated cytochrome c were removed by PD 10 Column and dialysis (MWCO 300, 000).
<Assessment of Peroxidase Activity of Cytochrome c Encapsulated in Disulfide-Containing Vesicle>

Figure 11:
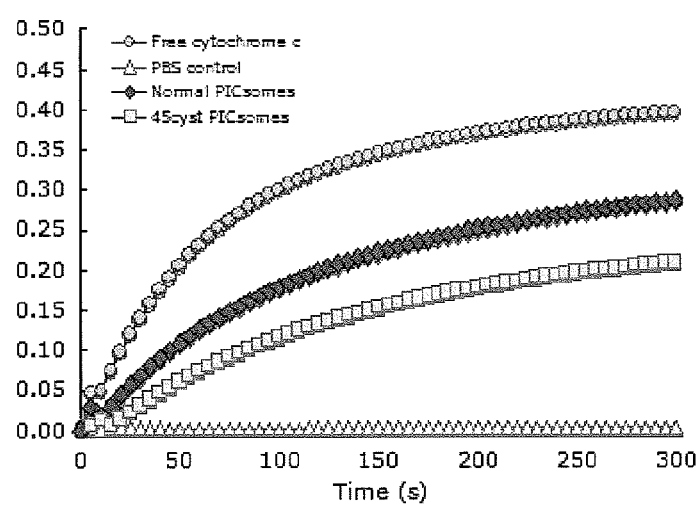
FIG. 11 shows the measurement results of peroxidase activity of cytochrome c-encapsulated vesicle.

The peroxidase activity of cytochrome c encapsulated in the 45cyst PICsome was assessed by change of absorbance (418 nm) after addition of $H_2O_2$ and ABTS solution. The assessment was carried out by adding 11.25 mM $H_2O_2$ solution and 0.9 mM ABTS solution to suspensions of the disulfide-containing 45cyst PICsome and a non-disulfide-containing Normal PICsome [(+) homo-P(Asp-AP)$_{82}$/(−) PEG-P(Asp)$_{75}$]. The results are shown in FIG. 11. The activity of cytochrome c encapsulated in the vesicle was confirmed regardless of the presence/absence of disulfide. This showed utility of the vesicle as a drug delivery system and a bioreactor.

INDUSTRIAL APPLICABILITY

The present invention provides an electrostatically bonded vesicle in which a disulfide bond has been introduced. The vesicle of the present invention can contain a substance such as compound inside a membrane of the vesicle, and therefore is useful as a drug delivery system and a material for various uses.

The invention claimed is:

1. A vesicle having a membrane which is formed from both a first polymer of (a) or (b) and a second polymer of (c) or (d) (with the proviso that a combination of (b) and (d) is excepted) and in which the cationic segment and anionic segment of the polymers are partially crosslinked by adding a crosslinking agent in an amount of 0.05 to 20 equivalents per equivalent of a carboxyl group in the anionic segment of the second polymer or 0.05 to 20 equivalents per equivalent of an amino group in the cationic segment of the first polymer, or in an amount of 0.05 to 20 equivalents of a thiol group in the cationic segment of the first polymer of the anionic segment of the second polymer, wherein the first polymer is: (a) a block copolymer (I) having both an electrically non-charged hydrophilic segment and a cationic segment; or (b) an amino acid polymer (I) having a cationic segment, and the second polymer is: (c) a block copolymer (II) having both an electrically non-charged hydrophilic segment and an anionic segment; or (d) an amino acid polymer (II) having an anionic segment, wherein a crosslinked site has a structure comprising disulfide bonds, wherein the cationic segment is represented by the following formula (1):

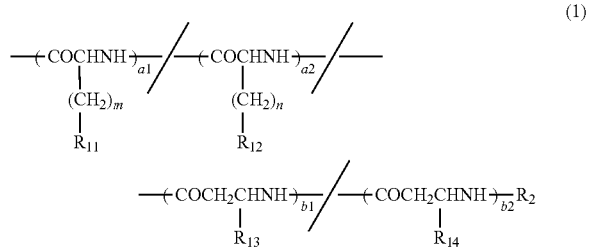

wherein: $R_2$ represents a hydrogen atom, an acetyl group, a trifluoroacetyl group, an acryloyl group or a methacryloyl group;

$R_{11}$ and $R_{13}$ each independently represent —$(CH_2)_3NH_2$ or —$CONH(CH_2)_s$—$X_1$, wherein: s is an integer from 0 to 20; and $X_1$ is at least one selected from the group consisting of —$NH_2$, a pyridyl group, a morpholyl group, a 1-imidazolyl group, a piperazinyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group, a piperidinyl group, a guanidino group, a diisopropylamino group, a dimethylamino group, a diethylamino group, —$(CH_2)_tNH_2$ and —$(NR_9(CH_2)_o)_pNHR_{10}$, wherein: $R_9$ represents a hydrogen atom or a methyl group; $R_{10}$ represents a hydrogen atom, an acetyl group, a trifluoroacetyl group, a benzyloxycarbonyl group, —C(=NH)—$NH_2$ or a tert-butoxycarbonyl group; o is an integer from 1 to 15; p is an integer from 1 to 5; and t is an integer from 0 to 15;

$R_{12}$ and $R_{14}$ each independently represent a thiol group, a $C_{1-12}$ alkyl group including a thiol group, —$SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —$CONH(CH_2)_s$—$X_2$, wherein: s is an integer from 0 to 20; and $X_2$ is at least one selected from the group consisting of a thiol group, a $C_{1-12}$ alkyl group including a thiol group, $SR_{30}$ ($R_{30}$ is the same as above), and a pyridyl group, a 1-imidazolyl group, a piperazinyl group, a 4-($C_{1-6}$ alkyl)-piperazinyl group, a 4-(amino $C_{1-6}$ alkyl)-piperazinyl group, a pyrrolidine-1-yl group, a N-methyl-N-phenylamino group and a piperidinyl group, which are substituted with a thiol group, a $C_{1-12}$ alkyl group including a thiol group or $SR_{30}$ ($R_{30}$ is the same as above), and —S—S—$(CH_2)_tNH_2$, —S—S—$(NR_9(CH_2)_o)_pNHR_{10}$, —$(CH_2)_tNHCO(CH_2)_uSH$ and —$(CH_2)_tNHC(=NH)(CH_2)_vSH$, wherein $R_9$, $R_{10}$, o, p and t are the same as above, u is an integer from 0 to 15, and v is an integer from 0 to 15;

m and n are 1 or 2;

a1 and a2 are an integer from 0 to 5,000, b1 and b2 are an integer from 0 to 5,000, and a1+a2+b1+b2 is 2 to 5,000; and "/" means that the sequence order of monomer units is arbitrary, and wherein the anionic segment is represented by the following formula (2):

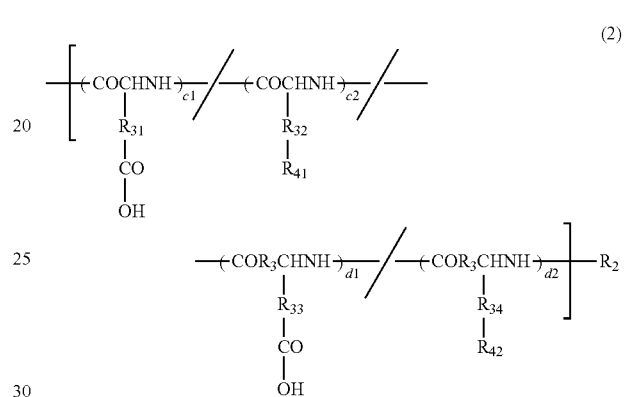

wherein: $R_2$ represents a hydrogen atom, an acetyl group, a trifluoroacetyl group, an acryloyl group or a methacryloyl group;

$R_3$s each independently represent a methylene group or an ethylene group;

$R_{31}$ and $R_{32}$ each independently represent a methylene group or an ethylene group;

$R_{33}$ and $R_{34}$ each independently represent a single bond, or a methylene group or an ethylene group;

$R_{41}$ and $R_{42}$ each independently represent a benzyloxycarbonyl group, a thiol group, a $C_{1-12}$ alkyl group including a thiol group, —$SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —$CONH(CH_2)_s$—$X_3$, wherein s is an integer from 0 to 20, and $X_3$ is a thiol group, a $C_{1-12}$ alkyl group including a thiol group or —$SR_{30}$ ($R_{30}$ is the same as above);

c1 and c2 are an integer from 0 to 5,000, d1 and d2 are an integer from 0 to 5,000, and c1+c2+d1+d2 is 2 to 5,000; and "/" means that the sequence order of monomer units is arbitrary.

2. The vesicle according to claim 1, wherein the membrane has a three-layer structure consisting of an outer layer, an intermediate layer and an inner layer, and wherein the outer layer and the inner layer are composed of the electrically non-charged hydrophilic segment and the intermediate layer is composed of the cationic segment and the anionic segment.

3. The vesicle according to claim 2, wherein the electrically non-charged hydrophilic segment of one of the block copolymers (I) and (II) forms the outer layer and the electrically non-charged hydrophilic segment of the other block copolymer forms the inner layer.

4. The vesicle according to claim 1, wherein the electrically non-charged hydrophilic segment is polyethylene glycol and/or poly(2-oxazoline), 5. The vesicle according to claim 1, wherein:
$R_{11}$ and $R_{13}$ are each independently —CONH(CH$_2$)$_s$—NH$_2$ (s is an integer from 2 to 8);
$R_{12}$ and $R_{14}$ are each independently a thiol group, —CONH(CH$_2$)$_s$—S—S(CH$_2$)$_t$NH$_2$, —CONH(CH$_2$)$_s$-SH, —CONH(CH$^2$)$_s$NHCO(CH$_2$)$_u$SH or —CONH(CH$^2$)$_s$NHC(=NH)(CH$^2$)$_v$SH (s is an integer from 2 to 8, t is an integer from 0 to 15, u is an integer from 1 to 8, and v is an integer from 1 to 8);
$R_2$ is a hydrogen atom;
a1 and a2 are an integer from 0 to 200, b1 and b2 are an integer from 0 to 200, and a1+a2+b1+b2 is 10 to 200.

6. The vesicle according to claim 1, wherein the block copolymer (I) is represented by the following formula (3) or (4):

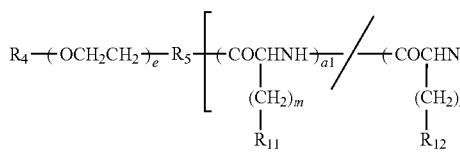
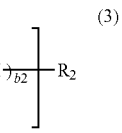

(3)

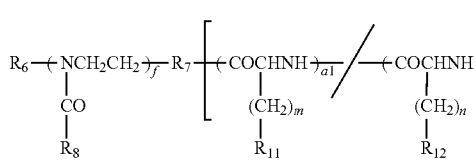
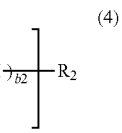

(4)

wherein: $R_2$ represents a hydrogen atom, an acetyl uoup, a trifluoroacetyl group, an acryloyl group or a methacryloyl group;
$R_{11}$ and $R_{13}$ each independently represent —(CH$_2$)$_3$NH$_2$ or —CONH(CH$_2$)$_s$—X$_1$, wherein: s is an integer from 0 to 20; and X$_1$ is at least one selected from the group consisting of —NH$_2$, a pyridyl group, a morpholyl group, a 1-imidazolyl group, a piperazinyl group, a 4-(C$_{1-6}$ alkyl)-piperazinyl group, a 4-(amino C$_{1-6}$ alkyl)-piperazinyl group, a pyrrolidine-1-yl group, a N-methyl-N-phenylamino group, a piperidinyl group, a guanidino group, a diisopropylamino group, a dimethylamino group, a diethylamino group, —(CH$_2$)$_t$NH$_2$ and —(NR$_9$(CH$_2$)$_o$)$_p$NHR$^{10}$, wherein: R$_9$ represents a hydrogen atom or a methyl group; R$_{10}$ represents a hydrogen atom, an acetyl group, a trifluoroacetyl group, a benzyloxycarbonyl group, —C(=NH)—NH$_2$ or a tert-butoxyearbonyl group; o is an integer from 1 to 15; p is an integer from 1 to 5; and t is an integer from 0 to 15;
$R_{12}$ and $R_{14}$ each independently represent a thiol group, a C$_{1-12}$ alkyl group including a thiol group, —SR$_{30}$ (R$_{30}$ represents a benzyl group, a 4-methoxybenzyl group, a 4-methylbenzyl group, a N-(acetyparninomethyl group, a ten-butyl group, a trityl group, a 2-pyridinesulfenyl group or a 3-nitro-2-pyridinesulfenyl group) or —CONH(CH$_2$)$_s$X$_2$, wherein: s is an integer from 0 to 20; and X$_2$ is at least one selected from the group consisting of a thiol group, a C$_{1-12}$ alkyl group including a thiol group, SR$_{30}$ (R$_{30}$ is the as above), and a pyridyl group, a 1-imidazolyl group, a piperazinyl group, a 4-(C$_{1-6}$ alkyl)-piperazinyi group, a 4-(amino C$_{1-6}$ alkyl)-piperazinyl group, a pyrrolidine-1-yl group, a N-methyl-N-phenylamino group and a piperidinyl group, which are substituted with a thiol group, a C$_{1-12}$ alkyl group including a thiol group or SR$_{30}$ (R$_{30}$ is the same as above), and —S—S—(CH$_2$)$_t$NH$_2$, —S—S—(NR$_9$(CH$_2$)$_o$)$_p$NHR$_{10}$, —(CH$_2$)$_t$NHCO(CH$_2$)$_u$SH and —(CH$_2$)$_t$NHC(=NH)(CH$_2$)$_v$SH, wherein R$_9$, R$_{10}$, o p and t are the same as above, u is an integer from 0 to 15, and v is an integer from 0 to 15;
m and n are 1 or 2;
$R_4$ represents a hydrogen atom or an optionally substituted linear or branched C$_{1-12}$ alkyl group;
$R_5$ represents —(CH$_2$)$_g$NH— and g is 0 to 5;
$R_6$ and $R_7$ are respectively the same as $R_4$ and $R_5$;
$R_8$ represents a linear or branched C$_{1-12}$ alkyl group;
a1 and a2 are an integer from 0 to 5,000, b1 and b2 are an integer from 0 to 5,000, and a1+a2+b1+b2 is 2 to 5,000;
e is an integer from 5 to 2,500, and f is an integer from 5 to 2,500; and
"/$_\leftrightarrows$" means that the sequence order of monomer units is arbitrary.

7. The vesicle according to claim 6, wherein:
$R_{11}$ and $R_{13}$ are each independently —CONH(CH$_2$)$_s$—NH$_2$ (s is an integer from 2 to 8);
$R_{12}$ and $R_{14}$ are each independently a thiol group, —CONH(CH$_2$)$_s$—S—S—(CH$_2$)$_t$NH$_2$, —CONH(CH$_2$)$_s$—SH, —CONH(CH$_2$)$_s$NHCO(CH$_2$)$_u$SH or —CONH(CH$_2$)$_s$NHC(=NH)(CH$_2$)$_v$SH (s is an integer from 2 to 8, t is an integer from 0 to 15, u is an integer from 1 to 8, and v is an integer from 1 to 8);
$R_2$ is a hydrogen atom;
$R_4$ is a methyl group;
a1 and a2 are an integer from 0 to 200, b1 and b2 are an integer from 0 to 200, and a1+a2+b1+b2 is 10 to 200, e is an integer from 10 to 300, and f is an integer from 10 to 300.

8. The vesicle according to claim 1, wherein the block copolymer (II) is represented by the following formula (5) or (6):

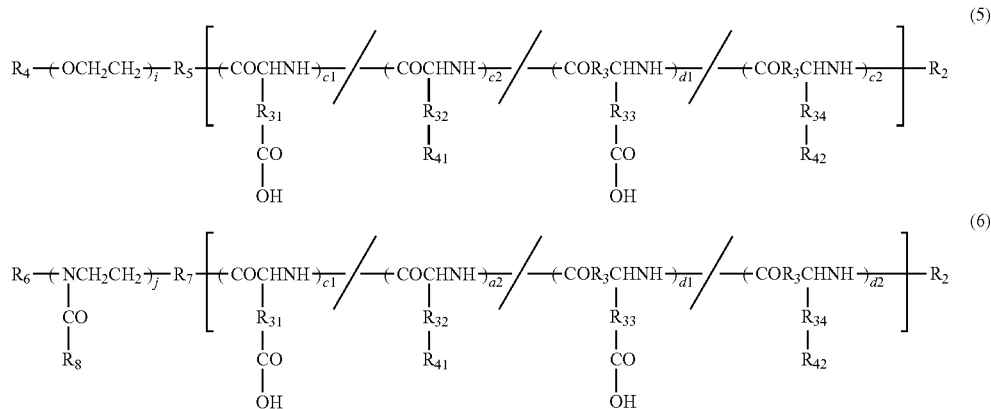

wherein: $R_2$ represents a hydrogen atom, an acetyl group, a trifluoroacetyl group, an acryloyl group or a methacryloyl group;

$R_3$s each independently represent a methylene group or an ethylene group;

$R_{31}$ and $R_{32}$ each independently represent a methylene group or an ethylene group;

$R_{33}$ and $R_{34}$ each independently represent a single bond, or a methylene group or an ethylene group;

$R_{41}$ and $R_{42}$ each independently represent a benzyloxycarbonyl group, a thiol group, a $C_{1-12}$ alkyl group including a thiol group, —$SR_{30}$ ($R_{30}$ represents a benzyl group, a 4-methoxybenzyl group, a 4-methylbenzyl group, a N-(acetyl)aminomethyl group, a tert-butyl group, a trityl group, a 2-pyridinesulfenyl group or a 3-nitro-2-pyridinesulfenyl group) or —$CONH(CH_2)_s$—$X_3$, wherein s is an integer from 0 to 20, and $X_3$ is a thiol group, a $C_{1-12}$ alkyl group including a thiol group or —$SR_{30}$ ($R_{30}$ is the same as above);

$R_4$ represents a hydrogen atom or an optionally substituted linear or branched $C_{1-12}$ alkyl group;

$R_5$ represents —$(CH_2)_gNH$— and g is an integer from 0 to 5;

$R_6$ and $R_7$ are respectively the same as $R_4$ and $R_5$;

$R_8$ represents a linear or branched $C_{1-12}$ alkyl group;

c1 and c2 are an integer from 0 to 5,000, d1 and d2 are an integer from 0 to 5,000, and c1+c2+d1+d2 is 2 to 5,000;

i and j are an integer from 5 to 2,500; and

"/" means that the sequence order of monomer units is arbitrary.

9. The vesicle according to claim 1, wherein the block copolymer (I) is represented by the formula (3) and the block copolymer (II) is represented by the formula (5).

10. The vesicle according to claim 1, which encapsulates a substance.

11. The vesicle according to claim 1, wherein the crosslinking agent 1-ethyl-3-(3-dimethylaminopropyl)carbodiimide (EDC)

12. The vesicle according to claim 1, wherein the crosslinking agent is 1,2-dithiane-t-4, t-5-diol r-1-oxide.

* * * * *